US012076409B2

(12) United States Patent
Camacho et al.

(10) Patent No.: US 12,076,409 B2
(45) Date of Patent: Sep. 3, 2024

(54) POLYMER-DRUG CONJUGATES FOR COMBINATION ANTICANCER THERAPY

(71) Applicant: The Regents of the University of California, Oakland, CA (US)

(72) Inventors: Kathryn M. Camacho, Los Angeles, CA (US); Stefano Menegatti, Raleigh, NC (US); Sunny Kumar, Aliso Viejo, CA (US); Douglas Vogus, Goleta, CA (US); Samir Mitragotri, Lexington, MA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 30 days.

(21) Appl. No.: 17/546,480

(22) Filed: Dec. 9, 2021

(65) Prior Publication Data
US 2022/0096645 A1  Mar. 31, 2022

Related U.S. Application Data

(60) Division of application No. 16/846,707, filed on Apr. 13, 2020, now Pat. No. 11,197,932, which is a continuation of application No. 15/556,798, filed as application No. PCT/US2016/021587 on Mar. 9, 2016, now Pat. No. 10,653,789.

(60) Provisional application No. 62/130,284, filed on Mar. 9, 2015.

(51) Int. Cl.
*A61K 47/61* (2017.01)
*A61K 31/4745* (2006.01)
*A61K 31/704* (2006.01)
*A61K 31/7068* (2006.01)

(52) U.S. Cl.
CPC .......... *A61K 47/61* (2017.08); *A61K 31/4745* (2013.01); *A61K 31/704* (2013.01); *A61K 31/7068* (2013.01)

(58) Field of Classification Search
CPC ... A61K 31/704; A61K 31/4745; A61K 47/61
See application file for complete search history.

(56) References Cited

U.S. PATENT DOCUMENTS

| | | | |
|---|---|---|---|
| 7,597,950 | B1 | 10/2009 | Stellacci et al. |
| 2005/0142178 | A1 | 6/2005 | Daftary et al. |
| 2008/0107722 | A1 | 5/2008 | Tardi et al. |
| 2008/0200428 | A1 | 8/2008 | Murano et al. |
| 2009/0197797 | A1 | 8/2009 | Norbedo et al. |
| 2010/0247620 | A1 | 9/2010 | Castor |
| 2011/0250284 | A1 | 10/2011 | Lavik et al. |
| 2012/0197060 | A1 | 8/2012 | Ray et al. |
| 2013/0022665 | A1 | 1/2013 | Nitsu et al. |
| 2014/0178462 | A1 | 6/2014 | Panzner et al. |

FOREIGN PATENT DOCUMENTS

| | | |
|---|---|---|
| EP | 0400610 A1 | 5/1990 |
| WO | 03028696 A2 | 4/2003 |
| WO | 2006003384 A1 | 1/2006 |
| WO | 2008121949 A1 | 10/2008 |
| WO | 2010129547 A1 | 11/2010 |
| WO | 2011112482 A2 | 9/2011 |
| WO | 2012142362 A2 | 10/2012 |
| WO | 2014194848 A1 | 12/2014 |

OTHER PUBLICATIONS

Dong et al., Med. Chem. Commun., 2012, 3, p. 1555-1561. (Year: 2012).*
Liao et al., J. Am. Chem. Soc., 2014, 136, p. 5896-5899, Published Apr. 11, 2014. (Year: 2014).*
Vasey et al. "Phase I clinical and pharmacokinetic study of PK1 [N-(2-hydroxypropyl) methacrylamide copolymer doxorubicin]: first member of a new class of chemotherapeutic agents—drug-polymer conjugates." Clinical Cancer Research 5(1): 83-94 (1999).
Vincent et al. "5-Fluorouracil selectively kills tumor-associated myeloid-derived suppressor cells resulting in enhanced T cell-dependent antitumor immunity." Cancer Research 70(8): 3052-3061 (2010).
Walton et al. "Constitutive expression of human Bcl-2 modulates nitrogen mustard and camptothecin induced apoptosis." Cancer Research 53(8): 1853-1861 (1993).
Wang et al. "Dexamethasone as a chemosensitizer for breast cancer chemotherapy: potentiation of the antitumor activity of adriamycin, modulation of cytokine expression, and pharmacokinetics." International Journal of Oncology 30(4): 947-953 (2007).
Wang et al. "Doxorubicin induces apoptosis in normal and tumor cells via distinctly different mechanisms intermediacy of H2O2-and p53-dependent pathways." Journal of Biological Chemistry 279(24): 25535-25543 (2004).
Wang et al. "Star-shape copolymer of lysine-linked di-tocopherol polyethylene glycol 2000 succinate for doxorubicin delivery with reversal of multidrug resistance." Biomaterials 33(28): 6877-6888 (2012).
Webb et al. "Randomized trial comparing epirubicin, cisplatin, and fluorouracil versus fluorouracil, doxorubicin, and methotrexate in advanced esophagogastric cancer." Journal of Clinical Oncology 15(1): 261-267 (1997).

(Continued)

*Primary Examiner* — Jonathan S Lau
(74) *Attorney, Agent, or Firm* — Nixon Peabody LLP; David S. Resnick; Nicole D. Kling

(57) ABSTRACT

Pharmaceutical compositions comprising two or more therapeutically active agents, such as two or more anticancer agents, conjugated to one or more biocompatible polymers, wherein the molar ratio of the agents and/or schedules of delivery provide a synergistic therapeutic effect, are described. Methods of making and using the pharmaceutical compositions are further described. In one embodiment, the pharmaceutical compositions contain topoisomerase I and topoisomerase II inhibitors conjugated to the same or different biocompatible polymers. The two or more anticancer agents are covalently coupled to the polymer(s), and thereby can be delivered to a tumor at a molar ratio which provides a synergistic effect. Optionally, the agents are coupled indirectly to the polymer(s) via a linker.

23 Claims, 12 Drawing Sheets

(56) References Cited

OTHER PUBLICATIONS

Weiss. "The Hill equation revisited: uses and misuses." The FASEB Journal 11(11): 835-841 (1997).
Wils et al. "Sequential high-dose methotrexate and fluorouracil combined with doxorubicin—a step ahead in the treatment of advanced gastric cancer: a trial of the European Organization for Research and Treatment of Cancer Gastrointestinal Tract Cooperative Group." Journal of Clinical Oncology 9(5): 827-831 (1991).
Xenidis et al. "A multicenter phase II study of pegylated liposomal doxorubicin in combination with irinotecan as second-line treatment of patients with refractory small-cell lung cancer." Cancer Chemotherapy and Pharmacology 68(1): 63-68 (2011).
Zelphati et al. "Mechanism of oligonucleotide release from cationic liposomes." Proceedings of the National Academy of Sciences 93(21): 11493-11498 (1996).
Zhong et al. "A novel liposomal vaccine improves humoral immunity and prevents tumor pulmonary metastasis in mice." International Journal of Pharmaceutics 399(1-2): 156-162 (2010).
Ishitsuka et al. "Role of uridine phosphorylase for antitumor activity of 5'-deoxy-5-fluorouridine." GANN Japanese Journal of Cancer Research 71(1): 112-123 (1980).
Jacquin et al. "Phase II trial of pegylated liposomal doxorubicin in combination with gemcitabine in metastatic breast cancer patients." American Journal of Clinical Oncology 35(1): 18-21 (2012).
Judson et al. "Randomised phase II trial of pegylated liposomal doxorubicin (DOXIL®/CAELYX®) versus doxorubicin in the treatment of advanced or metastatic soft tissue sarcoma: a study by the EORTC Soft Tissue and Bone Sarcoma Group." European Journal of Cancer 37(7): 870-877 (2001).
Julka et al. "A phase 2 study of sequential neoadjuvant chemotherapy with gemcitabine and doxorubicin followed by gemcitabine and cisplatin in patients with large or locally advanced operable breast cancer: results from long-term follow-up." Breast Cancer 20(4): 357-362 (2013).
Kaiser et al. "5-Fluorouracil in vesicular phospholipid gels for anticancer treatment: entrapment and release properties." International Journal of Pharmaceutics 256(1-2): 123-131 (2003).
Kalra et al. "Development of 5-FU and doxorubicin-loaded cationic liposomes against human pancreatic cancer: Implications for tumor vascular targeting." Pharmaceutical Research 23(12): 2809-2817 (2006).
Klein et al. "Prospective randomized trial using 5-fluorouracil, adriamycin and methotrexate (FAMTX) versus FAM for treatment of advanced gastric cancer." Oncology Research and Treatment 15(5): 364-367 (1992).
Klibanov et al. "Activity of amphipathic poly (ethylene glycol) 5000 to prolong the circulation time of liposomes depends on the liposome size and is unfavorable for immunoliposome binding to target." Biochimica et Biophysica Acta (BBA)-Biomembranes 1062(2): 142-148 (1991).
Krakoff. "Chemotherapy of gastrointestinal cancer." Cancer 30(6): 1600-1603 (1972).
Lammers et al. "Effect of physicochemical modification on the biodistribution and tumor accumulation of HPMA copolymers." Journal of Controlled Release 110(1): 103-118 (2005).
Lancet et al. "Phase 2 trial of CPX-351, a fixed 5: 1 molar ratio of cytarabine/daunorubicin, vs cytarabine/daunorubicin in older adults with untreated AML." Blood 123(21): 3239-3246 (2014).
Lashof-Sullivan et al., "Intravenous hemostats: challenges in translation to patients." Nanoscale 5(22):10719-10728 (2013).
Le et al. "Gemcitabine directly inhibits myeloid derived suppressor cells in BALB/c mice bearing 4T1 mammary carcinoma and augments expansion of T cells from tumor-bearing mice." International Immunopharmacology 9(7-8): 900-909 (2009).
Levchenko et al. "Liposome clearance in mice: the effect of a separate and combined presence of surface charge and polymer coating." International Journal of Pharmaceutics 240(1-2): 95-102 (2002).
Levi et al. "Analysis of a prospectively randomized comparison of doxorubicin versus 5-fluorouracil, doxorubicin, and BCNU in advanced gastric cancer: implications for future studies." Journal of Clinical Oncology 4(9): 1348-1355 (1986).
Liu et al. "Codelivery of doxorubicin and paclitaxel by cross-linked multilamellar liposome enables synergistic antitumor activity." Molecular Pharmaceutics 11(5): 1651-1661 (2014).
Liu et al. "Comparison of the therapeutic efficacy of 188Rhenium-liposomes and liposomal doxorubicin in a 4T1 murine orthotopic breast cancer model." Oncology Reports 27(3): 678-684 (2012).
Longley et al. "5-fluorouracil: mechanisms of action and clinical strategies." Nature Reviews Cancer 3(5): 330-338 (2003).
Longley et al. "5-Fluorouracil: Molecular Mechanisms of Cell Death." In R. Srivastava ed., Apoptosis, Cell Signaling, and Human Diseases: Molecular Mechanisms, vol. 1. Humana Press Inc. Chapter 11: 263-278 (2007).
Lyass et al. "Correlation of toxicity with pharmacokinetics of pegylated liposomal doxorubicin (Doxil) in metastatic breast carcinoma." Cancer: Interdisciplinary International Journal of the American Cancer Society 89(5): 1037-1047 (2000).
Lyseng-Williamson et al. "Pegylated liposomal doxorubicin: a guide to its use in various malignancies." BioDrugs 27(5): 533-540 (2013).
Macdonald et al. "5-Fluorouracil, doxorubicin, and mitomycin (FAM) combination chemotherapy for advanced gastric cancer." Annals of Internal Medicine 93(4): 533-536 (1980).
Maghsoudi et al. "5-Fluorouracil-loaded BSA nanoparticles: formulation optimization and in vitro release study." AAPS PharmSciTech 9(4): 1092-1096 (2008).
Maji et al. "A lipid based antigen delivery system efficiently facilitates MHC class-I antigen presentation in dendritic cells to stimulate CD8+ T cells." Scientific Reports 6(1): 1-12 (2016).
Markova et al. "Tautomeric equilibria of 5-fluorouracil anionic species in water." The Journal of Physical Chemistry A 114(50): 13154-13162 (2010).
Markovsky et al. "Anticancer polymeric nanomedicine bearing synergistic drug combination is superior to a mixture of individually-conjugated drugs." Journal of Controlled Release 187: 145-157 (2014).
Mastria et al. "Doxorubicin-conjugated polypeptide nanoparticles inhibit metastasis in two murine models of carcinoma." Journal of Controlled Release 208: 52-58 (2015).
Mayer et al. "Influence of vesicle size, lipid composition, and drug-to-lipid ratio on the biological activity of liposomal doxorubicin in mice." Cancer Research 49(21): 5922-5930 (1989).
Mayer et al. "Ratiometric dosing of anticancer drug combinations: controlling drug ratios after systemic administration regulates therapeutic activity in tumor-bearing mice." Molecular Cancer Therapeutics 5(7): 1854-1863 (2006).
Moghimi et al. "Stealth liposomes and long circulating nanoparticles: critical issues in pharmacokinetics, opsonization and protein-binding properties." Progress in Lipid Research 42(6): 463-478 (2003).
Muggia et al. "Phase II study of liposomal doxorubicin in refractory ovarian cancer: antitumor activity and toxicity modification by liposomal encapsulation." Journal of Clinical Oncology 15(3): 987-993 (1997).
Muggia et al. "Phase II trial of the pegylated liposomal doxorubicin in previously treated metastatic endometrial cancer: a Gynecologic Oncology Group study." Journal of Clinical Oncology 20(9): 2360-2364 (2002).
Murad et al. "Modified therapy with 5-fluorouracil, doxorubicin, and methotrexate in advanced gastric cancer." Cancer 72(1): 37-41 (1993).
O'Brien et al. "Reduced cardiotoxicity and comparable efficacy in a phase III trial of pegylated liposomal doxorubicin HCI (CAELYX™M/ Doxil®) versus conventional doxorubicin for first-line treatment of metastatic breast cancer." Annals of Oncology 15(3): 440-449 (2004).
Oommen et al. "Tallored doxorubicin-Hyaluronan conjugate as a potent anticancer glyco-D rug: an alternative to prodrug approach." Macromolecular Bioscience 14(3): 327-333 (2014).

(56) References Cited

OTHER PUBLICATIONS

Pavillard et al. "Effects of the combination of camptothecin and doxorubicin or etoposide on rat glioma cells and camptothecin-resistant variants." British Journal of Cancer 85(7): 1077-1083 (2001).
Pivkin et al., "Effect of red blood cells on platelet aggregation." IEEE Engineering in Medicine and Biology Magazine 28(2):32-37 (2009).
Platt et al "Anticancer therapeutics: targeting macromolecules and nanocarriers to hyaluronan or CD44, a hyaluronan receptor." Molecular Pharmaceutics 5(4): 474-486 (2008).
Ryan et al. "A phase I study of liposomal doxorubicin (Doxil) with topotecan." American Journal of Clinical Oncology 23(3): 297-300 (2000).
Safra et al. "Pegylated liposomal doxorubicin (doxil): reduced clinical cardiotoxicity in patients reaching or exceeding cumulative doses of 500 mg/m2." Annals of Oncology 11(8): 1029-1033 (2000).
Saito et al. "Stacking interaction between tryptophan and uracil in a synthetic model compound." Tetrahedron Letters 26(37): 4467-4470 (1985).
Song et al. "Amino acid ester prodrugs of the anticancer agent gemcitabine: synthesis, bioconversion, metabolic bioevasion, and hPEPT1-mediated transport." Molecular Pharmaceutics 2(2): 157-167 (2005).
Sugimoto et al. "Elevated expression of DNA topoisomerase II in camptothecin-resistant human tumor cell lines." Cancer Research 50(24): 7962-7965 (1990).
Sun et al. "Bioreducible PAA-g-PEG graft micelles with high doxorubicin loading for targeted antitumor effect against mouse breast carcinoma." Biomaterials 34(28): 6818-6828 (2013).
Szoka et al. "Comparative properties and methods of preparation of lipid vesicles (liposomes)." Annual Review of Biophysics and Bioengineering 9(1): 467-508 (1980).
Tardi et al. "Coencapsulation of irinotecan and floxuridine into low cholesterol-containing liposomes that coordinate drug release in vivo." Biochimica et Biophysica Acta (BBA)-Biomembranes 1768(3): 678-687 (2007).
Tardi et al. "In vivo maintenance of synergistic cytarabine: daunorubicin ratios greatly enhances therapeutic efficacy." Leukemia Research 33(1): 129-139 (2009).
Thurston et al. "Cationic liposomes target angiogenic endothelial cells in tumors and chronic inflammation in mice." The Journal of Clinical Investigation 101(7): 1401-1413 (1998).
Udhrain et al. "Pegylated liposomal doxorubicin in the treatment of AIDS-related Kaposi's sarcoma." International Journal of Nanomedicine 2(3): 345-352 (2007).
Vanhoefer et al. "Final results of a randomized phase III trial of sequential high-dose methotrexate, fluorouracil, and doxorubicin versus etoposide, leucovorin, and fluorouracil versus infusional fluorouracil and cisplatin in advanced gastric cancer: a trial of the European Organization for Research and Treatment of Cancer Gastrointestinal Tract Cancer Cooperative Group." Journal of Clinical Oncology 18(14): 2648-2657 (2000).
Andresen et al. "Advanced strategies in liposomal cancer therapy: problems and prospects of active and tumor specific drug release." Progress in Lipid Research 44(1): 68-97 (2005).
Anselmo et al., "Platelet-like nanoparticles: mimicking shape, flexibility, and surface biology of platelets to target vascular injuries." ACS Nano 8(11):11243-11253 (2014).
Arpicco et al. "Hyaluronic acid conjugates as vectors for the active targeting of drugs, genes and nanocomposites in cancer treatment." Molecules 19(3): 3193-3230 (2014).
Asselin et al., "Monomeric (glycine-proline-hydroxyproline) 10 repeat sequence is a partial agonist of the platelet collagen receptor glycoprotein VI." Biochemical Journal 339(Pt 2):413-418 (1999).
Bandyopadhyay et al. "Doxorubicin in combination with a small TGFβ inhibitor: a potential novel therapy for metastatic breast cancer in mouse models." PloS One 5(4): e10365 pp. 1-13 (2010).

Barenholz et al. "Doxil®—the first FDA-approved nano-drug: lessons learned." Journal of Controlled Release 160(2): 117-134 (2012).
Barenholz et al. "Stability of liposomal doxorubicin formulations: problems and prospects." Medicinal Research Reviews 13(4): 449-491 (1993).
Barenholz. "Liposome application: problems and prospects." Current Opinion in Colloid & Interface Science 6(1): 66-77 (2001).
Bennett et al. "Cationic lipids enhance cellular uptake and activity of phosphorothioate antisense oligonucleotides." Molecular Pharmacology 41(6): 1023-1033 (1992).
Buzzoni et al. "Adjuvant chemotherapy with doxorubicin plus cyclophosphamide, methotrexate, and fluorouracil in the treatment of resectable breast cancer with more than three positive axillary nodes." Journal of Clinical Oncology 9(12): 2134-2140 (1991).
Cabanes et al. "Comparative study of the antitumor activity of free doxorubicin and polyethylene glycol-coated liposomal doxorubicin in a mouse lymphoma model." Clinical Cancer Research 4(2): 499-505 (1998).
Cai et al. "Localized doxorubicin chemotherapy with a biopolymeric nanocarrier improves survival and reduces toxicity in xenografts of human breast cancer." Journal of Control Release 146(2): 212-218 (2010).
Campbell et al. "Cationic charge determines the distribution of liposomes between the vascular and extravascular compartments of tumors." Cancer Research 62(23): 6831-6836 (2002).
Cazap et al. "Phase II trials of 5-FU, doxorubicin, and cisplatin in advanced, measurable adenocarcinoma of the lung and stomach." Cancer Treatment Reports 70(6): 781-783 (1986).
Chang et al. "Biodistribution, pharmacokinetics and microSPECT/CT imaging of 188Re-bMEDA-liposome in a C26 murine colon carcinoma solid tumor animal model." Anticancer Research 27(4B): 2217-2225 (2007).
Charrois et al. "Multiple injections of pegylated liposomal Doxorubicin: pharmacokinetics and therapeutic activity." Journal of Pharmacology and Experimental Therapeutics 306(3): 1058-1067 (2003).
Chen et al. "Hyaluronic acid-based drug conjugates: state-of-the-art and perspectives." Journal of Biomedical Nanotechnology 10(1): 4-16 (2014).
Cheung et al. "AIDS-related Kaposi's sarcoma: a phase II study of liposomal doxorubicin." Clinical Cancer Research 5(11): 3432-3437 (1999).
Chou et al. "Quantitative analysis of dose-effect relationships: the combined effects of multiple drugs or enzyme inhibitors." Advances in Enzyme Regulation 22: 27-55 (1984).
"Chou. ""Theoretical basis, experimental design, and computerized simulation of synergism and antagonism in drug combination studies.""Pharmacological Reviews 58(3): 621-681 (2006)".
Coller et al., "Thromboerythrocytes. In vitro studies of a potential autologous, semi-artificial alternative to platelet transfusions." The Journal of Clinical Investigation 89(2):546-555 (1992).
Cullinan et al. "A comparison of three chemotherapeutic regimens in the treatment of advanced pancreatic and gastric carcinoma: fluorouracil vs fluorouracil and doxorubicin vs fluorouracil, doxorubicin, and mitomycin." Jama 253(14): 2061-2067 (1985).
Da Costa et al. "Encapsulation of 5-fluorouracil in liposomes for topical administration." Acta Scientiarum Technol Maringá 25: 53-61 (2003).
Debnath et al. "Amino and carboxy functionalized modified nucleosides: a potential class of inhibitors for angiogenin." Bioorganic Chemistry 52: 56-61 (2014).
Diasio et al. "Clinical pharmacology of 5-fluorouracil." Clinical Pharmacokinetics 16(4): 215-237 (1989).
Doshi et al., "Platelet mimetic particles for targeting thrombi in flowing blood." Advanced Materials 24(28):3864-3869 (2012).
Du et al. "Quercetin greatly improved therapeutic index of doxorubicin against 4T1 breast cancer by its opposing effects on HIF-1α in tumor and normal cells." Cancer Chemotherapy and Pharmacology 65(2): 277-287 (2010).
Duggan et al. "Pegylated liposomal doxorubicin." Drugs 71(18): 2531-2558 (2011).

(56) References Cited

OTHER PUBLICATIONS

Duncan. "Development of HPMA copolymer-anticancer conjugates: clinical experience and lessons learnt." Advanced Drug Delivery Reviews 61(13): 1131-1148 (2009).

Duncan. "Polymer conjugates as anticancer nanomedicines." Nature Reviews Cancer 6(9): 688-701 (2006).

Ellerhorst et al. "Phase II trial of doxil for patients with metastatic melanoma refractory to frontline therapy." Oncology Reports 6(5): 1097-1106 (1999).

Friend et al. "Endocytosis and intracellular processing accompanying transfection mediated by cationic liposomes." Biochimica et Biophysica Acta (BBA)-Biomembranes 1278(1): 41-50 (1996).

Gabizon. "Pegylated liposomal doxorubicin: metamorphosis of an old drug into a new form of chemotherapy." Cancer Investigation 19(4): 424-436 (2001).

Gabra et al. "Weekly doxorubicin and continuous infusional 5-fluorouracil for advanced breast cancer." British Journal of Cancer 74(12): 2008-2012 (1996).

Gallois et al. "Comparison of the interaction of doxorubicin, daunorubicin, idarubicin and idarubicinol with large unilamellar vesicles: circular dichroism study." Biochimica et Biophysica Acta (BBA)-Biomembranes 1370(1): 31-40 (1998).

Giuliani et al. "New doxorubicin analogs active against doxorubicin-resistant colon tumor xenografts in the nude mouse." Cancer Research 40(12): 4682-4687 (1980).

Goebel et al. "Efficacy and safety of Stealth liposomal doxorubicin in AIDS-related Kaposi's sarcoma." British Journal of Cancer 73(8): 989-994 (1996).

Gordon et al. "Recurrent epithelial ovarian carcinoma: a randomized phase III study of pegylated liposomal doxorubicin versus topotecan." Journal of Clinical Oncology 19(14): 3312-3322 (2001).

Grant et al. "Single-agent chemotherapy trials in small-cell lung cancer, 1970 to 1990: the case for studies in previously treated patients." Journal of Clinical Oncology 10(3): 484-498 (1992).

Greco et al. "Combination therapy: opportunities and challenges for polymer-drug conjugates as anticancer nanomedicines." Advanced Drug Delivery Reviews 61(13): 1203-1213 (2009).

Gubala et al., "Kinetics of immunoassays with particles as labels: effect of antibody coupling using dendrimers as linkers." Analyst 136(12):2533-2541 (2011).

Gubala et al., "Kinetics of immunoassays with particles as labels: effect of antibody coupling using dendrimers as linkers." Analyst 136(12):2533-2541 (2011) [Electronic Supplemental Information, 3 pages].

Gubernator. "Active methods of drug loading into liposomes: recent strategies for stable drug entrapment and increased in vivo activity." Expert Opinion on Drug Delivery 8(5): 565-580 (2011).

Halford et al. "A phase II study evaluating the tolerability and efficacy of CAELYX (liposomal doxorubicin, Doxil) in the treatment of unresectable pancreatic carcinoma." Annals of Oncology 12(10): 1399-1402 (2001).

Hansen et al. "Continuous 5-fluorouracil infusion in refractory carcinoma of the breast." Breast Cancer Research and Treatment 10(2): 145-149 (1987).

Harada et al. "A phase I/II trial of irinotecan plus amrubicin supported with G-CSF for extended small-cell lung cancer." Japanese Journal of Clinical Oncology 44(2): 127-133 (2014).

Haran et al. "Transmembrane ammonium sulfate gradients in liposomes produce efficient and stable entrapment of amphipathic weak bases." Biochimica et Biophysica Acta (BBA)-Biomembranes 1151(2): 201-215 (1993).

Harrington et al. "Biodistribution and pharmacokinetics of 111 In-DTPA-labelled pegylated liposomes in a human tumour xenograft model: implications for novel targeting strategies." British Journal of Cancer 83(2): 232-238 (2000).

Hortobagyi et al. "Evaluation of high-dose versus standard FAC chemotherapy for advanced breast cancer in protected environment units: a prospective randomized study." Journal of Clinical Oncology 5(3): 354-364 (1987).

International Search Report for corresponding PCT application PCT/US2016/021587 mailed Jun. 16, 2016.

\* cited by examiner

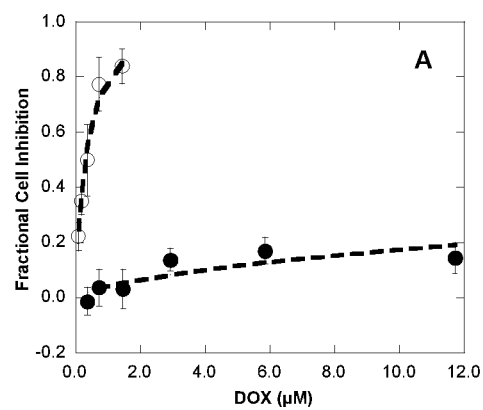
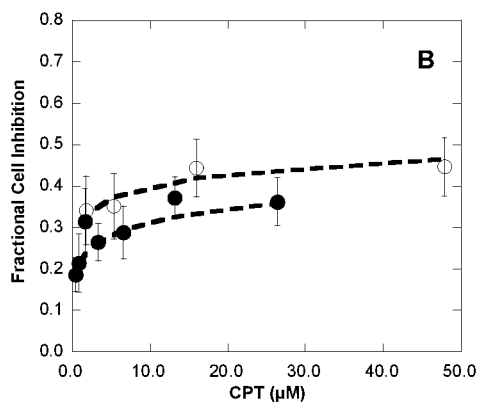
FIG. 3A  FIG. 3B
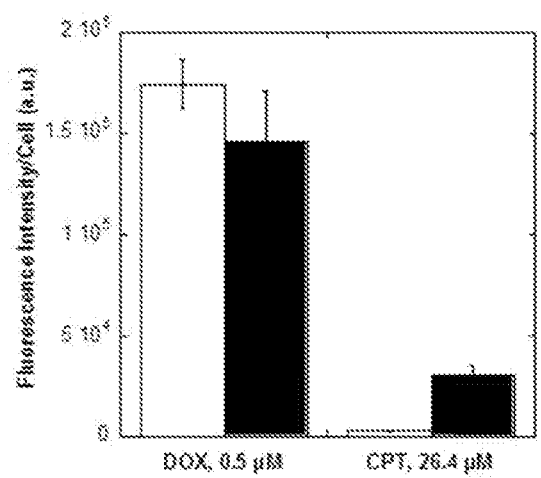
FIG.4

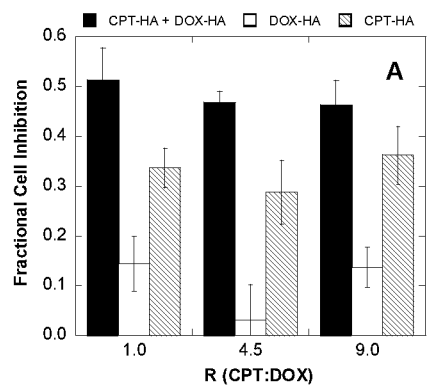
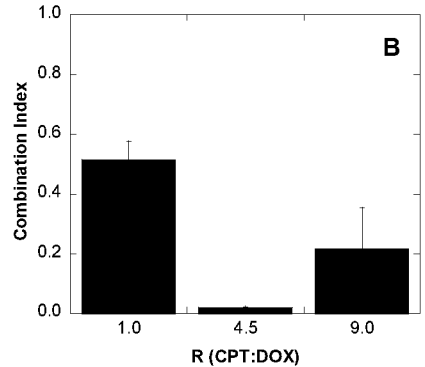
FIG. 5A                FIG. 5B
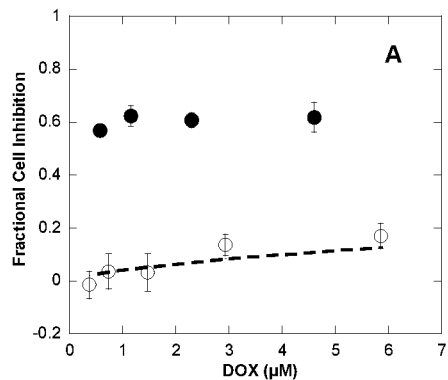
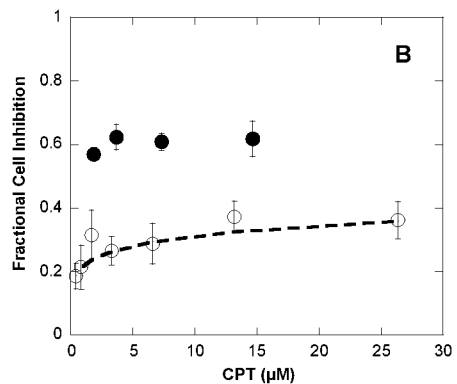
FIG. 6A                FIG. 6B

POLYMER-DRUG CONJUGATES FOR COMBINATION ANTICANCER THERAPY

CROSS-REFERENCE TO RELATED APPLICATIONS

This application is a divisional under 35 U.S.C. § 121 of co-pending U.S. application Ser. No. 16/846,707 filed Apr. 13, 2020; which is a continuation under 35 U.S.C. § 120 of U.S. application Ser. No. 15/556,798 filed Sep. 8, 2017 issued as U.S. Pat. No. 10,653,789 on May 19, 2020; which is a U.S. National Stage under 35 U.S.C. § 371 of International Application No. PCT/US2016/021587 filed Mar. 9, 2016; which claims benefit under 35 U.S.C. § 119(e) of U.S. Provisional Application No. 62/130,284 filed on Mar. 9, 2015, the contents of which are incorporated herein by reference in their entireties.

STATEMENT REGARDING FEDERALLY SPONSORED RESEARCH

This invention was made with government support under Grant No. DGE-1144085 awarded by the National Science Foundation and Grant No. 1 S10 OD010610-01A1 awarded by the National Institutes of Health. The government has certain rights in the invention.

FIELD OF THE INVENTION

The invention generally relates to pharmaceutical compositions and methods of delivering therapeutically active agents to a patient, particularly for the treatment of cancer.

BACKGROUND OF THE INVENTION

Topoisomerases I and II are nuclear enzymes that are involved in DNA replication and are targets for anticancer therapy. Clinically useful antitumor drugs such as camptothecin, irinotecan and topotecan interfere with the function of topoisomerase I (Top I). Antitumor drugs, such as doxorubicin, daunorubicin, etoposide, teniposide, amrubicin and amsacrine, inhibit topoisomerase II (Top II). Numerous efforts have focused on identifying efficacious and safe combination therapies of Top I and II inhibitors. These efforts are attributed to the collateral drug sensitivity of the enzymes. Top I inhibitor exposed cancer cells compensate the obstruction of DNA replication by enhancing Top II activity. This effect further sensitizes cancer cells to Top II inhibitors (Sugimoto, et al., Cancer Res, 1990. 50(24): 7962-5).

Some combination therapies of topoisomerase I and II inhibitors have been shown to inhibit cancer cell growth in vitro. However, clinical studies of these combinations have not progressed beyond phase II trials for several reasons. For example, doxorubicin provided a >20% overall response rate in patients with small cell lung cancer (Grant, et al., J Clin Oncol, 1992. 10(3): 484-98). However, when doxorubicin was administered with irinotecan, the combination showed no improvement in efficacy, providing only a 12.9% overall response in patients (Xenidis, et al., Cancer Chemother Pharmacol, 2011. 68(1): 63-8). The combination of amrubicin and irinotecan improved overall response up to 67% but elicited severe hematological toxicity in 71% of patients (Harada, et al., Jpn J Clin Oncol, 2014. 44(2): 127-33). Further, a clinical trial of topotecan and pegylated liposomal doxorubicin was terminated due to dose-limiting toxicity and the inability to arrive at a tolerable combination dose (Ryan, et al., Am J Clin Oncol, 2000. 23(3): 297-300). The results of clinical combinations of Top I and II inhibitors typically fall within one of two categories: little to no improvement in therapeutic efficacy; or augmented toxicity compared to the single drug counterparts.

Polymer-drug conjugates have been explored for the administration of single chemotherapy agents and can have clinical benefits over the drug administered alone (Duncan, Adv Drug Deliv Rev, 2009. 61(13): 1131-48). Clinical benefits may include reduced liver accumulation, enhanced drug localization in tumors, and improved pharmacokinetics (Vasey, et al., Clin Cancer Res, 1999. 5(1): 83-94). Conjugation of an anticancer drug to a polymer can improve clinical efficacy by promoting drug accumulation in tumors rather than in organs via the enhanced permeation and retention effect (Lammers, et al., J Control Release, 2005. 110(1): 103-18). This method ensures that tumors are exposed to effective amounts of the drug combination.

While some drug conjugates have been prepared and evaluated, they need further improvements to yield superior efficacies (R. Duncan, Adv Drug Delivery Revs vol. 61, 2009), Thus, there exists the need for anticancer therapies that are effective in treating cancer with reduced side effects.

It is an object of the invention to provide improved pharmaceutical compositions for delivering two or more therapeutic agents to a patient in need of treatment, and particularly, for reducing or preventing tumor growth in a cancer patient while limiting toxicity from the active agent.

It is yet another object of the invention to provide improved methods of treating cancer in a patient, and more particularly to reduce or prevent tumor growth in a cancer patient with reduced side effects from the same drugs typically delivered alone.

It is another object of the invention to provide improved pharmaceutical compositions for delivering to a patient two or more therapeutically active agents.

It is yet another object of the invention to provide methods for making these compositions.

SUMMARY OF THE INVENTION

The pharmaceutical compositions described herein contain two or more drugs in the form of polymer-drug conjugates. Polymer-drug conjugates allow one to modify the ratio between drugs using stoichiometry and/or to modify the schedule of delivery (i.e. release of the drug from the polymer-drug conjugate). A desired schedule of delivery for each drug in the pharmaceutical composition can be achieved by varying the bond strength of the bond between the drug and the polymer or the bond strength of the bond in a linker used to conjugate the drug to the polymer to achieve a synergistic effect when two or more drugs are delivered.

Pharmaceutical compositions containing two or more anticancer agents conjugated to one or more biocompatible polymers, wherein the molar ratio of the agents, the schedule of delivery, or both, provide a synergistic therapeutic effect, are described. The biocompatible polymer, or at least one of the polymers, is preferably each of the polymers, is preferably a water-soluble, biocompatible polymer. Methods of making and using the pharmaceutical compositions are further described.

In some embodiments, the pharmaceutical compositions contain two or more anticancer agents conjugated to the same biocompatible polymer at a molar ratio, schedule of delivery, or both which provide a synergistic effect compared to delivering each of the agents alone. In other embodiments, the pharmaceutical compositions contain two or more anticancer agents, where at least a first agent is conjugated to a first biocompatible polymer, and at least a second agent is conjugated to a second biocompatible polymer, at a molar ratio, schedule of delivery, or both provide a synergistic effect compared to delivering each of the agents alone, where the first and second polymers are the same or different. Preferably, the polymer, or at least one of the polymers, is hyaluronic acid. In some embodiments, the anticancer agents are topoisomerase I inhibitors, topoisomerase II inhibitors, or both. The two or more agents are covalently coupled directly or indirectly (e.g. via a linker) to the polymer or polymers, and thereby can be delivered to a site in need of treatment, such as a tumor in a cancer patient.

Further described are pharmaceutical compositions containing two or more therapeutically active agents conjugated to a biocompatible polymer, wherein the molar ratio of the agents, the schedule of delivery, or both provide a synergistic therapeutic effect. Methods of making and using the pharmaceutical compositions are further described.

In some embodiments, the pharmaceutical compositions contain two or more therapeutically active agents conjugated to the same biocompatible polymer at a molar ratio, schedule of delivery, or both which provide a synergistic effect compared to delivering each of the agents alone. In other embodiments, the pharmaceutical compositions contain two or more therapeutically active agents, where at least a first agent is conjugated to a first biocompatible polymer, and at least a second agent is conjugated to a second biocompatible polymer, at a molar ratio, schedule of delivery, or both which provide a synergistic effect compared to delivering each of the agents alone, where the first and second polymers are the same or different. Preferably, the polymer, or at least one of the polymers, is hyaluronic acid. In some embodiments, the therapeutically active agents are anticancer agents. In some embodiments, the therapeutically active agents are not anticancer agents. The two or more agents are covalently coupled directly or indirectly (e.g. via a linker) to the polymer or polymers, and thereby can be delivered to a site in need of treatment.

The pharmaceutical compositions can be formulated by any suitable method for any suitable method of administration. Exemplary methods for forming the polymer-drug conjugates are described herein. Suitable dosage forms for parenteral administration include, but are not limited to, solutions, suspensions, and emulsions. Suitable oral dosage forms include, but are not limited to, tablets, capsules, solutions, suspensions, emulsions, syrups, and lozenges. Suitable dosage forms for intranasal include, but are not limited to, solutions, suspensions, and emulsions. Optionally, the compositions can be administered to and through a mucosal site.

The compositions are effective at treating a variety of diseases or disorders, such as cancers.

BRIEF DESCRIPTION OF THE DRAWINGS

FIGS. 3A and 3B display the cell inhibition of human breast cancer cell line BT-474 in the presence of DOX in free solution (open circles) or DOX-HA (filled circles, FIG. 3A) and CPT in free solution (open circles) or CPT-HA (closed circles, FIG. 3B).

FIG. 4 is a bar graph showing the quantitative fluorescence of DOX or CPT in free solution (white bars) or as a HA-conjugate form (black bars) present in BT-474 cells after 24 hours of incubation at 37° C. and 5% $CO_2$.

FIG. 5A is a bar graph showing cell inhibition of human breast cancer cell line BT-474 treated with combinations of CPT-HA and DOX-HA at various molar ratios (black bars). Single HA-conjugate treatments of DOX-HA (white) and CPT-HA (hatched) at concentrations which make-up the combination are juxtaposed for direct comparison. FIG. 5B displays the combination Index (CI) values calculated for the CPT-HA and DOX-HA combinations shown in FIG. 5A.

FIG. 6A displays the cell inhibition of BT-474 cells in the presence of DOX-HA (open circles) or CPT-HA-DOX conjugates (filled circles). FIG. 6B displays the comparison of the cell inhibition of CPT-HA (open circles) and CPT-HA-DOX conjugates of R=3.2 CPT:DOX (filled circles).

FIG. 10A compares the cell fraction cell inhibition of DOX-HA (blank circles) and CPT-HA-DOX (filled circles). FIG. 10B compares the fraction cell inhibition of CPT-HA (blank circles) and CPT-HA-DOX (filled circles).

FIG. 11A shows the fractional cell inhibition for the doxorubicin (DOX, at 0.3 μM) and paclitaxel (PAC, at 0.005 μM) pair. Drug sequence for the DOX to PAC switch is shown as blank squares, PAC to DOX switch is shown as filled circles. FIG. 11B shows the fractional cell inhibition for the PAC (0.005 μM) and IXA (0.015 μM) pair. Drug sequence for the PAC to IXA switch is shown as blank squares, IXA to PAC switch is shown as filled circles. FIG. 11C shows the fractional cell inhibition for the DOX (0.3 μM) and GEM (0.2 μM) pair. Drug sequence for the GEM to DOX switch is shown as blank squares, DOX to GEM is shown as filled circles.

FIG. 12A shows the schedule of DOX (patterned bars) and GEM (solid black bars) as a function of time (days). FIG. 12B shows the effect of schedule on fractional cell inhibition. Fractional cell inhibition is shown as patterned columns, solid black columns, and solid white columns for DOX, GEM, and the combination of DOX/GEM, respectively, for the schedules shown in FIG. 12A. FIG. 12C shows combination index as a function of the schedules of DOX and GEM shown in FIG. 12A.

FIG. 14A shows the schedule of PAC (patterned bars) and LAP (solid black bars) as a function of time (days). FIG. 14B shows combination index as a function of the schedules of delivery for PAC and LAP shown in FIG. 14A.

FIG. 15A shows the conjugation of a drug (R), such as DOX, GEM, or another agent via the vicinal hydroxyl groups on carbons two and three of the glucuronic acid monomer. FIG. 15B shows the conjugation of a drug (R), such as DOX, GEM, or another agent via the carboxylic acid group of the glucuronic acid via a hydrazine functional group. FIG. 15C shows the conjugation of a drug (R), such as DOX, GEM, or another agent via the carboxylic acid group of the glucuronic acid via an amide functional group.

In FIG. 16A, the prodrug is formed by reacting the 3'-hydroxyl group of the deoxyribose with the carboxylic acid of glycine. In FIG. 16B, the prodrug is formed by reacting the primary amine of gemcitabine with the carboxylic acid of glycine. In FIG. 16C, the prodrug is formed by reacting the 5'-hydroxyl group of the deoxyribose with the carboxylic acid of glycine.

DETAILED DESCRIPTION OF THE INVENTION

I. Definitions

Figures 1A, 1B, 1C, 1D:
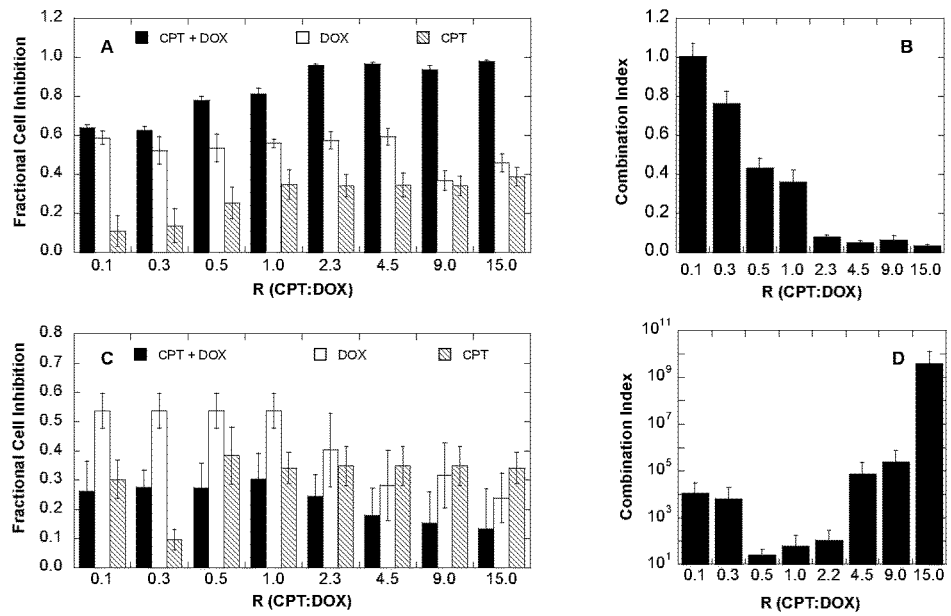
FIGS. 1A and 1C are bar graphs showing the cell inhibition of human breast cancer cell line BT-474 and mouse brain endothelial cell line bEnd.3, respectively, treated with combinations of camptothecin (CPT, hatched) and doxorubicin (DOX, white) at various molar ratios (black bars).
FIGS. 1B and 1D display the combination index (CI) values for the CPT and DOX combinations in BT-474 and bEnd.3 cells, respectively.

The term "bond strength" is a measure of the bond dissociation energy between two atoms or more atoms. When the atoms are covalently bonded, the bond strength refers to the bond dissociation energy between two atoms.

The term "conjugate," as it relates to polymer-drug conjugate refers to two or more molecular structures that are linked by a direct or indirect covalent or non-covalent bond. Non-covalent interactions include, but are not limited to, electrostatic interactions, hydrogen bonding interactions, van der Waals interactions, dipole-dipole interactions, π-π stacking, magnetic interactions, and metal coordination. Preferably, the conjugation is via covalent bonds.

The term "treating" or "treatment", as used herein, indicates that the method has, at the least, mitigated abnormal cellular proliferation. For example, the method can reduce the rate of cancer growth in a patient, or prevent the continued growth of a cancer, or even reduce the overall reach of the cancer "Biocompatible", as used herein, generally refers to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

"Water soluble polymer", as used herein, means a polymer having a solubility of at least 1 mg/liter in water or monophasic aqueous-organic mixtures, at 37° C. and standard pressure.

As used herein "synergistic therapeutic effect" refers to a therapeutic effect that is greater than additive for the particular combination of drugs as determined using the combination index (CI) analysis.

The term "schedule of drug delivery" or "schedule of delivery" refers to the time of release of a therapeutically active agent, such as an anticancer agent, from its formulation. More specifically, it refers to the time of release of a therapeutically active agent, such as an anticancer agent, from a polymer-drug conjugate.

The terms "therapeutic agent," "therapeutically active agent," and "drug" are used interchangeably herein, and refer to an agent that can be administered to prevent, treat or ameliorate one or more symptoms of a disease or disorder.

The term "therapeutically effective amount" refers to an amount of the therapeutically active agent that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

II. Pharmaceutical Compositions

The pharmaceutical compositions contain two or more anticancer agents conjugated to the same or different biocompatible polymers at a molar ratio, schedule of delivery, or both which provide a synergistic effect compared to delivering each of the agents alone.

A desired schedule of delivery for each drug in the pharmaceutical composition can be achieved by varying the bond strength of the bond between the drug and the polymer or the bond strength of the bond in a linker used to conjugate the drug to the polymer to achieve a synergistic effect when two or more drugs are delivered. For example, a first drug in the pharmaceutical composition can be attached to a polymer via a first linker or covalent bond having a first bond strength and a second drug in the pharmaceutical composition can be attached to either the same or a different polymer via a second linker or covalent bond having a second bond strength. The first and second bond strengths can be the same or different. For pharmaceutical compositions containing more than two drugs, the pharmaceutical composition can similarly have additional linkers or covalent bonds between the additional drugs and the same or different polymers to which the first and second drugs are attached, where each of the additional linkers or covalent bonds has a bond strength that is the same as or different from either or both of the first and second bond strengths.

In some embodiments, two or more anticancer agents are conjugated to the same biocompatible polymer. In other embodiments, at least a first agent is conjugated to a first biocompatible polymer, and at least a second agent is conjugated to a second biocompatible polymer, where the first and second polymers are the same or different. Preferably, the polymer, or at least one of the polymers, is hyaluronic acid.

The two or more anticancer agents are conjugated directly or indirectly, via linkers, to the backbone or side chains of one or more polymers. The strengths of the bonds involved in direct conjugation, and the strengths of the bonds in the linkers, may be the same, different, or a combination thereof (i.e. some of the bond strengths are the same while others are different). In some embodiments, the side chains have the same or different chemical moieties. The bond strengths of the bonds, directly conjugating the two or more anticancer agents to the polymers are the same, different, or a combination thereof (i.e. some of the bond strengths are the same while others are different). The bond strengths of the bonds indirectly conjugating the two or more anticancer agents via linkers are the same, different, or a combination thereof (i.e. some of the bond strengths are the same while others are different). For example, when the bonds or linkers have the same bond strength, each of the anticancer agents is connected to the polymer via the same bond or the same linker. When the bonds or linkers have different bond strengths, each of the anticancer agents is connected to the polymer via a different bond or different linker.

For pharmaceutical compositions containing at least three different anticancer agents, the bond strengths of the bonds in the linkers that indirectly conjugate the two or more anticancer agents or the bond strengths of the bonds the directly conjugate are the same, different, or a combination thereof (i.e. some of the bond strengths are the same while others are different). some of the bond strengths may the same, while others may be different. For example, the bonds conjugating, directly or indirectly, a first anticancer agent and a second anticancer agent to one or more polymers, can have the same bond strength, while the bonds conjugating, directly or indirectly, a third anticancer agent to the one or more polymers have a different bond strength than the bonds conjugating the first and second anticancer agents to the one or more polymers.

Preferably, the bond strengths of the bonds conjugating directly or indirectly, via linkers, the two or more anticancer agents to the one or more polymers are different. The bonds or bonds in the linkers are cleaved at the same or different rates, or a combination thereof (i.e. some bonds are cleaved at one rate and others are cleaved at another rate). Preferably, the bonds or bonds in the linker are cleaved at different rates.

In some embodiments, the pharmaceutical compositions contain two or more therapeutically active agents coupled to each other via conjugation to the same biocompatible polymer at a molar ratio which provides a synergistic effect compared to delivering each of the agents alone. In other embodiments the molar ratios of the therapeutically active agents coupled to each other via conjugation to the same biocompatible polymer, schedule of delivery, or both provide a synergistic effect, compared to delivering each of the therapeutically active agents alone. Preferably, the polymer is hyaluronic acid.

In other embodiments, the pharmaceutical compositions contain two or more therapeutically active agents, where a first agent is conjugated to a first biocompatible polymer, and a second agent is conjugated to a second biocompatible polymer, at a molar ratio which provides a synergistic effect compared to delivering each of the agents alone, where the first and second biocompatible polymers are the same or different polymers. In other embodiments the molar ratios of the therapeutically active agents conjugated to a first and a second biocompatible polymer, schedule of delivery, or both provide a synergistic effect, compared to delivering each of the therapeutically active agents alone. Preferably, the polymer, or at least one of the polymers, is hyaluronic acid.

In some embodiments, the therapeutically active agents are topoisomerase I inhibitors, topoisomerase II inhibitors, or both.

The two or more therapeutically active agents are conjugated to the polymer or polymers directly to the backbone or side chains, or they are conjugated indirectly via linkers. In some embodiments, the side chains have the same or different chemical moieties. The bond strengths of the bonds, directly conjugating the two or more therapeutically active agents to the polymers are the same, different, or a combination thereof (i.e. some of the bond strengths are the same, while others are different). The bond strengths of the bonds indirectly conjugating the two or more therapeutically active agents via linkers are the same, different, or a combination thereof (i.e. some of the bond strengths are the same while others are different). In some embodiments, the strengths of the bonds involved in direct conjugation, and the strengths of the bonds in the linkers, are the same, different, or a combination thereof (i.e. some of the bond strengths are the same while others are different). For example, when the bonds or linkers have the same bond strength, each of the therapeutically active agents is connected to the polymer via the same bond or the same linker. When the bonds or linkers have different bond strengths, each of the therapeutically active agents is connected to the polymer via a different bond or different linker. Typically, three or more different therapeutically active agents are present in embodiments in which the bond strengths are both the same and different. In these embodiments, the bonds conjugating, directly or indirectly, a first therapeutically active agent and a second therapeutically active agent to the one or more polymers, have the same bond strength, while the bonds conjugating, directly or indirectly, a third therapeutically active agent to the one or more polymers have a different bond strength than the bonds conjugating the first and second therapeutically active agents to the one or more polymers. Preferably, the bond strengths of the bonds conjugating directly or indirectly, via linkers, the two or more therapeutically active agents to the one or more polymers are different. The bonds or bonds in the linkers are cleaved at the same or different rates, or a combination thereof (i.e. some bonds are cleaved at a first rate and others a cleaved at a second, different rate or more than one different rates). Preferably, the bonds or bonds in the linker are cleaved at different rates.

A. Therapeutically Active Agents

Pharmaceutical compositions comprising two or more therapeutically active agents conjugated to a biocompatible polymer, wherein the molar ratio of the agents, the schedule of delivery, or both provide a synergistic therapeutic effect, are described. The therapeutically active agent may be any drug providing a therapeutic or prophylactic effect in vivo. The drug is selected based on the disease or disorder to be treated or prevented.

As used herein references to a therapeutically active agent or anticancer agent include the biologically acceptable salts of the agent. For example references herein to doxorubicin, gemcitabine, and/or lapatinib, are also references to their biologically acceptable salts, such as doxorubicin hydrochloride salt, gemcitabine hydrochloride salt, and lapatinib di-p-toluenesulfonate salt, respectively.

Examples of therapeutically active agents include, but are not limited to, nucleic acids, nucleic acid analogs, small molecules, peptidomimetics, proteins, peptides, carbohydrates or sugars, lipids, or surfactants, or a combination thereof.

Drugs contemplated for use in the pharmaceutical compositions described herein include, but are not limited to, the following categories and examples of drugs and alternative forms of these drugs such as alternative salt forms, free acid forms, free base forms, and hydrates: analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); antiasthamatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline); antidiabetics (e.g., biguanides and sulfonylurea derivatives); antifungal agents (e.g., griseofulvin, ketoconazole, itraconizole, amphotericin B, nystatin, and candicidin); antihypertensive agents (e.g., propranolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, propranolol, isometheptene mucate, and dichloralphenazone); sedatives/hypnotics (e.g., barbiturates such as pentobarbital, pentobarbital, and secobarbital; and benzodiazapines such as flurazepam hydrochloride, triazolam, and midazolam); antianginal agents (e.g., beta-adrenergic blockers; calcium channel blockers such as nifedipine, and diltiazem; and nitrates such as nitroglycerin, isosorbide dinitrate, pentaerythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine); antiarthritic agents (e.g., phenylbutazone, sulindac, penicillamine, salsalate, piroxicam, azathioprine, indomethacin, meclofenamate, gold sodium thiomalate, ketoprofen, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibrinolytic agents (e.g., aminocaproic acid); hemorheologic agents (e.g., pentoxifylline); antiplatelet agents (e.g., aspirin); anticonvulsants (e.g., valproic acid, divalproex sodium, phenytoin, phenytoin sodium, clonazepam, primidone, phenobarbitol, carbamazepine, amobarbital sodium, methsuximide, metharbital, mephobarbital, mephenytoin, phensuximide, paramethadione, ethotoin, phenacemide, secobarbitol sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, and methdilazine); agents useful for calcium regulation (e.g., calcitonin, and parathyroid hormone); antibacterial agents (e.g., amikacin sulfate, aztreonam, chloramphenicol, chloramphenicol palmitate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate; steroidal compounds, hormones and hormone analogues (e.g., incretins and incretin mimetics such as GLP-1 and exenatide, androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium); hypoglycemic agents (e.g., human insulin, purified beef insulin, purified pork insulin, recombinantly produced insulin, insulin analogs, glyburide, chlorpropamide, glipizide, tolbutamide, and tolazamide); hypolipidemic agents (e.g., clofibrate, dextrothyroxine sodium, probucol, pravastitin, atorvastatin, lovastatin, and niacin); peptides; proteins (e.g., DNase, alginase, superoxide dismutase, and lipase); nucleic acids (e.g., sense or anti-sense nucleic acids encoding any therapeutically useful protein, including any of the proteins described herein, and siRNA); agents useful for erythropoiesis stimulation (e.g., erythropoietin); antiulcer/anti-reflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); oil-soluble vitamins (e.g., vitamins A, D, E, K, and the like); as well as other drugs such as mitotane, halonitrosoureas, anthrocyclines, and ellipticine.

A description of these and other classes of useful drugs and a listing of species within each class can be found in Martindale, The Extra Pharmacopoeia, 30th Ed. (The Pharmaceutical Press, London 1993), the disclosure of which is incorporated herein by reference in its entirety.

1. Topoisomerase I and Topoisomerase II Inhibitors

In one embodiment, the composition contains a combination of one or more topoisomerase I inhibitors and one or more topoisomerase II inhibitors. In some embodiments, these active agents are anti-cancer agents.

A topoisomerase I inhibitor is a therapeutically active agent that is capable of inhibiting the DNA re-ligation enzymatic reaction catalyzed by topoisomerase I. Topoisomerase I inhibitors create a stabilized DNA-topoisomerase I complex sufficient to inhibit the reaction. Topoisomerase I inhibitors include, but are not limited to, plant alkaloids, plant alkaloid derivatives, camptothecin, irinotecan, topotecan, and analogs thereof. In preferred embodiments, the topoisomerase I inhibitor is camptothecin.

Likewise, a topoisomerase II inhibitor is a therapeutically active agent that is capable of inhibiting the DNA re-ligation enzymatic reaction catalyzed by topoisomerase II. Topoisomerase II inhibitors include, but are not limited to doxorubicin, bleomycin, daunorubicin, epirubicin, mitomycin and actinomycin. In preferred embodiments, the topoisomerase II inhibitor is doxorubicin.

2. Anticancer Agents

In one embodiment, the pharmaceutical composition contains a combination of two or more anticancer drugs, preferably at least one of the anticancer drugs is a topoisomerase I inhibitor and at least a one of the anticancer drugs is topoisomerase II inhibitor.

Additional anticancer agent(s), or other therapeutically active agent(s), may be coupled to the first and/or second anticancer agent via conjugation to the same polymer as the first and/or the second anticancer agent, or to another biocompatible polymer.

Suitable additional anticancer drugs include, but are not limited to, antineoplastics such as ixabepilone, gemcitabine and derivatives thereof, lapatinib, cyclophosphamide, methotrexate, fluorouracil, carboplatin, carmustine (BCNU), methyl-CCNU, cisplatin, etoposide, phenesterine, paclitaxel and derivatives thereof, docetaxel and derivatives thereof, vinblastine, vincristine, tamoxifen, and piposulfan.

Preferably, the anticancer agents are doxorubicin and derivatives thereof, paclitaxel and derivatives thereof, gemcitabine and derivatives thereof, docetaxel and derivatives thereof, camptothecin, ixabepilone, or lapatinib.

3. Other Therapeutically Active Agents

In some embodiments, the therapeutically active agents are anticancer agents. In some embodiments, the therapeutically active agents are not anticancer agents. Additional therapeutically active agents include, but are not limited to, peptides, antibodies, and immune stimulating agents.

B. Polymers

In some embodiments, the therapeutically active agents are coupled to each other by covalently attaching directly or indirectly (e.g. via a linker) to a biocompatible polymer, such as a water-soluble, biocompatible polymer which contains carboxylic acid, hydroxyl, amine, or thiol, functional groups, or combinations thereof.

In other embodiments, the active agents are not coupled to each other, rather a first active agent is coupled to a first polymer via a covalent bond directly or indirectly (e.g. via a linker), and a second active agent is coupled to a second polymer via a covalent bond directly or indirectly (e.g. via a linker), where the first and second polymers are the same or different. In embodiments where two or more of the active agents are not coupled to each other, but are coupled to the same polymer, the term "same polymer" refers to different molecules of polymers that have the same repeat units regardless of the molecular weight. For example, the first polymer could be hyaluronic acid of a particular molecule weight and the second polymer could be hyaluronic acid of the same or a different molecule weight relative to the first polymer.

If more than two agents are present in the pharmaceutical composition, the additional agents may be attached to additional polymers, or may be attached to the first or the second polymer.

In some embodiments, in place of covalent bonds, the two or more therapeutically active agents attached to the one or more biocompatible polymers via non-covalent interactions.

The polymer is preferably non-toxic, non-immunogenic and is readily excreted from living organisms. Optionally, the polymer is biodegradable. Preferably the polymer is a water-soluble polymer, optionally the polymer contains carboxylic acid, hydroxyl, amine, or thiol functional groups, or combinations thereof.

Polymers containing functional groups that react with hydroxy, amino, or sulfhydryl groups or groups that are capable of being converted to functional groups that react with hydroxy, amino, or sulfhydryl groups can be used to prepare the conjugates described herein. Alternatively, the polymer can contain nucleophilic groups, such as hydroxyl, amino, or thiol groups, which react with electrophilic groups on each of the active agents.

Suitable polymers include, but are not limited to, hyaluronic acid (HA), poly(vinyl alcohol) (PVA), poly(N-(2-hydroxypropyl)methacrylamide) (HPMA), poly(isobutylene-alt-maleic anhydride) (PIBMA), poly(aspartic acid), poly(glutamic acid), polylysine, poly(acrylic acid), alginic acid, chitosan, carboxymethyl cellulose, carboxymethyl dextran, polyethyleneimine, polyesters, and blends and copolymers thereof.

The polymers typically have a molecular weight of 1,000 to 1,000,000 Daltons, preferably 10,000 to 1,000,000 Daltons. In one embodiment, the polymer is hydrolytically degradable. In preferred embodiments, the polymer is hyaluronic acid.

C. Linkers

The two or more therapeutically active agents, such as two or more anticancer agents, may be conjugated indirectly, via linkers, to the backbone or side chains of the one or more biocompatible polymers.

The linkers (or a portion thereof) or one or more of the bonds between an agent and a linker may be cleaved at the same rate or a different rate as the cleavage of another linker or one or more of the bonds between a different agent and another linker in the pharmaceutical composition. Cleavage can occur by any suitable mechanism, such as via hydrolysis, enzymatic cleavage, the application of thermal energy, photoenergy, or a combination thereof.

The linkers may be homo-bifunctional or hetero-bifunctional. In some instances, combinations of homo-bifunctional linkers and hetero-bifunctional linkers are used.

Examples of homo-bifunctional linkers include, but are not limited to adipic acid dihydrazide, amino acids such as glycine, aldehydes such as ethanedial, pyruvaldehyde, 2-formyl-malonaldehyde, glutaraldehyde, adipaldehyde, heptanedial, octanedial; di-glycidyl ether, diols such as 1,2-ethanediol, 1,3-propanediol, 1,4-butanediol, 2,3-butanediol, 1,5-pentanediol, benzene-1,4-diol, 1,6-hexanediol, tetra(ethylene glycol) diol), PEG, di-thiols such as 1,2-ethanedithiol, 1,3-propanedithiol, 1,4-butanedithiol, 2,3-butanedithiol, 1,5-pentanedithiol, benzene-1,4-dithiol, 1,6-hexanedithiol, tetra(ethylene glycol) dithiol), diamine such as ethylene diamine, propane-1,2-diamine, propane-1,3-diamine, N-methylethylenediamine, N,N'-dimethylethylenediamine, pentane-1,5-diamine, hexane-1,6-diamine, spermine and spermidine, divinyladipate, divinylsebacate, diamine-terminated PEG, double-ester PEG-N-hydroxysuccinimide, and di-isocyanate-terminated PEG. In a preferred embodiment, the homo-bifunctional linker is adipic acid dihydrazide.

Examples of hetero-bifunctional linkers include, but are not limited to, epichlorohydrin, S-acetylthioglycolic acid N-hydroxysuccinimide ester, 5-azido-2-nitrobenzoic acid N-hydroxysuccinimide ester, 4-azidophenacyl bromide, bromoacetic acid N-hydroxysuccinimide ester, N-(3-dimethylaminopropyl)-N'-ethylcarbodiimide, Iodoacetic acid N-hydroxysuccinimide ester, 4-(N-mMaleimido)benzophenone 3-(2-pyridyldithio)propionic acid N-hydroxysuccinimide ester 3-maleimidobenzoic acid N-hydroxysuccinimide ester, N,N'-cystamine-bis-acrylamide, N,N'-methylene-bis-acrylamide and N,N'-ethylene-bis-acrylamide.

D. Ratios of Active Agents

The relative amount of each active agent in the pharmaceutical composition is selected to provide a synergistic effect when the combination of the drugs is delivered together in the formulation.

Suitable ratios of the active agents in the formulation for providing a synergistic effect can be determined using Chou and Talalay's Combination Index (CI). (Chou, T. C., Pharmacol Rev, 2006. 58(3): p. 621-81). In this analysis, the active agents of interest are combined in a variety of molar ratios (R) to assess for synergy.

The combination index (CI) theorem offers quantitative definition for additive effect (CI=1), synergism (CI<1), and antagonism (CI>1) in drug combinations, where synergism is more than an additive effect and antagonism is less than an additive effect.

For example, for a formulation containing two drugs, the derived combination index equation is:

$$CI = \frac{(D)_1}{(D_z)_1} + \frac{(D)_2}{(D_x)_2} = \frac{(D)_1}{(D_m)_1[f_a/(1-f_a)]^{1/m_1}} + \frac{(D)_2}{(D_m)_2[f_a/(1-f_a)]^{1/m_2}} \qquad \text{Eq. I}$$

As used in Equation I, D is the dose (or concentration of a drug); fa is fraction affected by D and can be used to describe, for example, fractions of cells whose growth was inhibited, factional tumor volume reduction or other drug targets which were inhibited due to drug exposure; $D_m$ is the median-effect dose (e.g., $IC_{50}$); and m is the coefficient signifying the shape of the dose-effect relationship. $(Dx)_1$ is for $(D)_1$ "alone" that inhibits a system x %, and $(Dx)_2$ is for $(D)_2$ "alone" that inhibits a system x % whereas in the numerator, $(D)_1+(D)_2$, "in combination" also inhibit x %. Note that the denominators of the last two terms are the expression of the median-effect equation (MEE).

The CI Value quantitatively defines synergism (CI<1), additive effect (CI=1) and antagonism (CI>1).

Molar ratios can be derived from studies in in vitro experiments. As disclosed in Example 2, the molar ratios for the combination of camptothecin and doxorubicin were assessed in BT-474 or bEnd.3 cells. Combination Index (CI) decreased with increasing molar ratio (R) of drugs, with the greatest synergy occurring when R (CPT:DOX)>2 (i.e., 0.01<CI<0.08).

The molar ratios of the agents range from about 1:1 to about 1:1000. All integer pairs, rational number pairs, or integer and rational number pairs of molar ratios between 1:1 and 1:1000 are specifically contemplated and disclosed. In some aspects, the ranges of the molar ratios are selected with the proviso that the CI is less than one. In addition, all ranges defined by any pair of these molar ratios are also specifically contemplated and disclosed. For example, in some embodiments, the ratio for the paclitaxel:doxorubicin pair (PAC:DOX) is between about 1:1 and about 1:100, preferably 1:60; the ratio for the doxorubicin:gemcitabine pair (DOX:GEM) is between about 1:1 and about 1:10, preferably 1:1.3.

E. Schedule of Drug Delivery

The polymer-drug conjugates in the pharmaceutical compositions may allow for the different drugs to be released from the formulation at the same time, or at different times to achieve a synergistic effect. In some embodiments, the drugs are released at different times.

For drug delivery schedules that involve simultaneous release of the drug, the drugs may be conjugated to the same or different polymers. Preferably the drugs are conjugated to the same polymer directly via bonds or indirectly via linkers that are cleaved at the same rate. Preferably the drugs are coupled to each other via conjugation to the same polymer (i.e. the same molecule). Cleavage can occur via hydrolysis, enzymatic cleavage, the application of thermal energy, photoenergy, or combinations thereof.

When the drug delivery schedules involve release of the drugs at different times after the pharmaceutical composition is administered to a patient, the drugs are conjugated to the same or different polymers using bonds or linkers that are cleaved at different rates. Cleavage can occur via hydrolysis, enzymatic cleavage, the application of thermal energy, photoenergy, or combinations thereof. Following administration of a pharmaceutical composition containing one or more polymer-drug conjugates, the different drugs are released at schedules that differ by seconds, minutes, hours, days, weeks, months or years. Preferably, the schedules of drug delivery differ by hours, or within a week, most preferably hours or days. Typically, the second drug is released within 24 hours, 36 hours, or 48 hours of the release of the first drug. For example, following administration of a pharmaceutical composition containing one or more polymer-drug conjugates, a first polymer-drug conjugate having a first drug starts releasing its drug after a first period of time following administration. After a second period of time following administration, a second polymer-drug conjugate having a second drug starts releasing the second drug after the second period of time. In each of the first and second polymer-drug conjugates, the time of release of the drug (schedule of delivery) can be varied as needed to achieve the desired synergistic effect.

In some embodiments, the drug delivery schedules for the different drugs in a particular pharmaceutical composition are the same, i.e. each of the drugs is released at the same time.

F. Dosage Forms

The pharmaceutical compositions can be in any suitable form for administration. In some embodiments, the dosage form is a parenteral dosage form. In certain embodiments, the compositions are administered locally, for example, by injection directly into a site to be treated (e.g., into a tumor). In others, the pharmaceutical composition is provided in an enteral dosage form. Suitable oral dosage forms include, but are not limited to, tablets, capsules, solutions, suspensions, emulsions, syrups, and lozenges. Suitable dosage forms for transmucosal administration (intranasal, vaginal, rectal, or sublingual) include but are not limited to, solutions, suspensions, and emulsions.

a. Parenteral Dosage Forms

Suitable parenteral dosage forms include, but are not limited to, solutions, suspension, and emulsions. In some embodiments, the pharmaceutical composition is injected directly into the tumor site.

Formulations for parenteral administration may contain one or more pharmaceutically acceptable excipients including, but not limited to, surfactants, salts, buffers, pH modifying agents, emulsifiers, preservatives, anti-oxidants, osmolality/tonicity modifying agents, and water-soluble polymers.

The emulsion is typically buffered to a pH of 3-8 for parenteral administration upon reconstitution. Suitable buffers include, but are not limited to, phosphate buffers, acetate buffers, and citrate buffers.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium azide, sodium benzoate, sodium propionate, benzalkonium chloride, benzethonium chloride, benzyl alcohol, cetypyridinium chloride, chlorobutanol, phenol, phenylethyl alcohol, and thimerosal.

b. Dosages

Suitable dosages for each pharmaceutical composition can be determined by known methods. For example, suitable dosages for parenterally administered pharmaceutical compositions containing at least one top I inhibitor and at least one top II inhibitor bound to one or more biocompatible polymers range from 1-300 mg/m$^2$. The dosage can also be expressed as mg of drug per kilogram of body weight (mg/kg). In mg/kg, the dose is preferably ≤50 mg/kg. The dosage can also be expressed as the mole percent (mol %) of active drug in the polymer-drug conjugate. In mol %, the active drug forms ≤20 mol % of the polymer formulation. The dose is also expressed as a concentration, such as picomolar (pM), nanomolar (nM), or micromolar (μM). Expressed as micromolar (μM), the dose of each therapeutically active agent or anticancer agent is between about between 0.001 μM and about 10 between about 0.001 μM and about 5 between about 0.001 μM and about between about 0.001 and about 0.5 μM. Preferably, the doses of each therapeutically active agent or anticancer agent is between about 0.001 μM and about 10 μM.

III. Methods of Manufacture

The compositions described herein can be prepared by covalently attaching any of therapeutically active agents or derivatives thereof, such as the anticancer agents or derivatives thereof, to a water-soluble, biocompatible polymer. For example, the anticancer agents (or therapeutically active agents) to be coupled to the polymer are activated using a variety of chemistries known in the art to form reactive derivatives. In some embodiments, the anticancer agents or therapeutically active agents already contain functional groups that do not require activation prior to conjugating to the polymer. The reactive derivative of the anticancer agent (or therapeutically active agent) is reacted with the polymer to covalently link the agents to the polymer. The reactive derivative can contain a nucleophilic or electrophilic group which reacts with a corresponding electrophilic group or nucleophilic group, respectively, on the polymer. The anticancer agents or therapeutically active agents are conjugated directly to the polymers or indirectly via linkers.

In general, the anticancer agents or other therapeutically active agents are conjugated to the polymers via various bonds to modify the rate of release of the drugs. For instance in the case of hyaluronic acid, coupling of an amine group at the carboxyl functional group of the glucuronic acid residue has been reported, (Oomen, et al., Macromolecular Bioscience 2014, 14, 327-333), the contents of which are incorporated herein by reference. An anticancer agent or other therapeutically active agent, containing a suitable group, such as an amine, can be conjugated to the hyaluronic acid via the formation of an amide bond. In addition, the vicinal diol groups at carbon-2 and carbon-3 of the glucuronic acid residue can be oxidized using a suitable oxidizing agent, such as sodium periodate, to form aldehydes. The aldehydes can be reacted with a suitable group, such as an amine, on an anticancer agent or therapeutically active agent to conjugate the drug to the polymer via an imine bond.

Further, a bifunctional linker can be used to conjugate the drug to the polymer, (Cai, et al., Journal of Controlled Release 2010, 146(2), 212-218), the contents of which are incorporated herein by reference. Briefly, a homo-bifunctional linker, such as adipic acid dihydrazide, reacts with the carboxyl group of hyaluronic acid to form a hydrazone, while the anticancer agent or other therapeutically active agent reacts with the free end of the unreacted linker to conjugate the drug to the polymer.

Figure 16A:
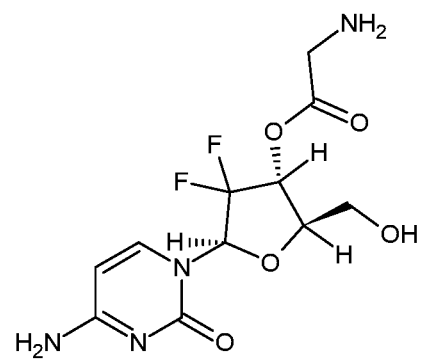
FIGS. 16A-16C are chemical structures of different GEM-glycine prodrugs.

Further, the anticancer agent or other therapeutically active agent can be reacted with a suitable molecule to form a prodrug. For example, gemcitabine can be reacted with amino acids to form gemcitabine-amino acid esters (Song, et al., Molecular Pharmaceutics 2005, 2(2), 157-167), the contents of which are incorporated herein by reference. For example, the carboxyl group of glycine can react with the hydroxyl group at the 3' hydroxyl group of the deoxyribose ring of gemcitabine to form an ester bond (see, e.g. FIG. 16A). Other exemplary prodrugs of gemcitabine are described in Example 8 and depicted in FIGS. 16B and 16C. The prodrug is then conjugated to a polymer, such as hyaluronic acid, via a suitable functional group on the prodrug.

One of ordinary skill in the art will understand that these are merely illustrative examples, and other anticancer agents or therapeutically active agents can be modified in a similar manner, or other mechanisms for binding an agent to a polymer or linker can be used to prepare the polymer-drug conjugates.

IV. Methods of Use and Administration

The compositions described herein can be used to treat cancer in a patient. Cancers to be treated include, but are not limited to, breast cancer (e.g., metastatic or locally advanced breast cancer), prostate cancer (e.g., hormone refractory prostate cancer), renal cell carcinoma, lung cancer (e.g., small cell lung cancer and non-small cell lung cancer (including adenocarcinoma, squamous cell carcinoma, bronchoalveolar carcinoma and large cell carcinoma)), pancreatic cancer, gastric cancer (e.g., gastroesophageal, upper gastric or lower gastric cancer), colorectal cancer, squamous cell cancer of the head and neck, ovarian cancer (e.g., advanced ovarian cancer, platinum-based agent resistant or relapsed ovarian cancer), lymphoma (e.g., Burkitt's, Hodgkin's or non-Hodgkin's lymphoma), leukemia (e.g., acute myeloid leukemia) and gastrointestinal cancer.

In one embodiment, one or more adverse side effects are reduced compared to the delivery of the same amount of a combination of the therapeutically active agents, such as topoisomerase I and II inhibitors, in an unconjugated form. In some embodiments, the adverse side effect is hematological toxicity.

EXAMPLES

The present invention may be further understood by reference to the following non-limiting examples.

Example 1. Synthesis of Hyaluronic Acid Conjugates

Materials and Methods

Camptothecin (CPT), N-(3-Dimethylaminopropyl)-N'-ethylcarbodiimide hydrochloride (EDC), 4-(dimethylamino) pyridine (DMAP), ethylenediamine, Tween-80 and rhodamine B (RhoB) were purchased from Sigma-Aldrich (St. Louis, MO, USA). Doxorubicin (DOX) was obtained from LC Laboratories (Woburn, MA, USA). Hyaluronic acid (HA) of 250 kDa MW was purchased from Creative PEGWorks (Winston Salem, NC, USA). Sephadex G-25 PD-10 columns were obtained from GE Healthcare Life Sciences (Piscataway, NJ, USA).

CPT and DOX were conjugated to HA via nucleophilic acyl substitution according to the procedures in Scheme 1.

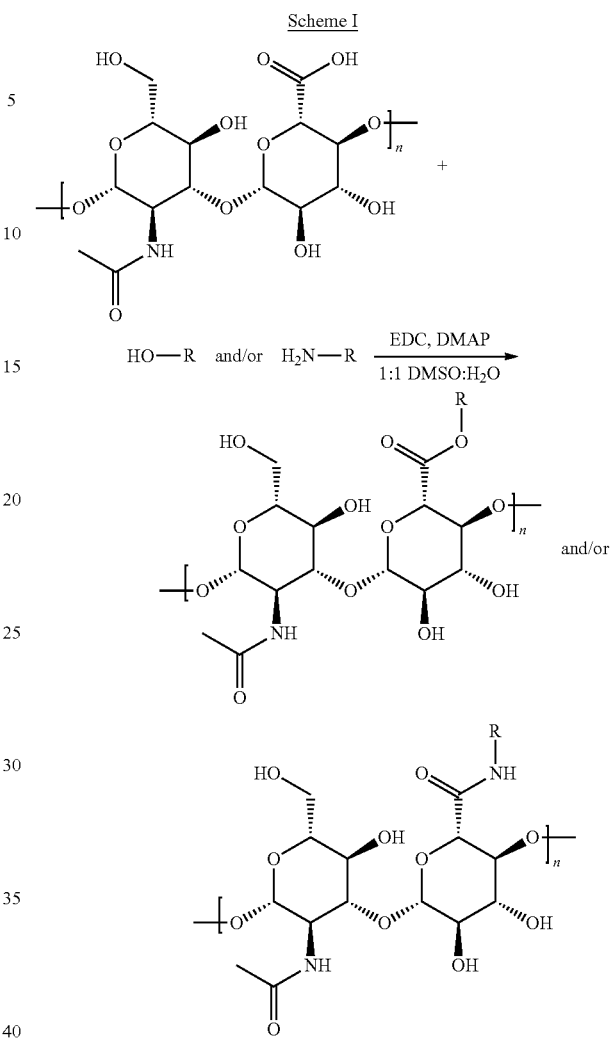

CPT-conjugation was achieved via ester formation (Lee, et al., Bioconjug Chem, 2008. 19(6): p. 1319-25) to the carboxylic acid moieties on hyaluronic acid or aminolysis for DOX-conjugation (Minko, et al., Int J Cancer, 2000. 86(1): 108-17). For each reaction, 100 mg of 250 kDa MW HA was dissolved in a 10 mL mixture of DMSO/water (1:1 by volume) under stirring and slight heating (40° C.). DMAP and EDC were added at a molar ratio of 0.75:1 relative to HA, and were allowed to activate the polymer for 1 hour under stirring. For CPT-conjugated HA (CPT-HA), CPT was slowly added to the reaction mixture at a molar ratio of 0.4:1 CPT:HA. For DOX-conjugated HA (DOX-HA), DOX was dissolved in the reaction mixture in a molar ratio of 0.2:1 DOX:HA.

CPT and DOX-conjugated HA (CPT-HA-DOX) was synthesized by treating CPT to HA for 3 days, followed by coupling of DOX to CPT-HA. The reactions proceeded at 40° C. CPT-HA and DOX-HA were separated from unreacted free drugs, EDC and DMAP via size exclusion chromatography through Sephadex G-25 PD-10 desalting columns (5000 MW exclusion limit) equilibrated in phosphate buffered saline (PBS, pH 7.4). The reaction products were concentrated in 0.5 mL centrifugal filter tubes (3000 NMWL) for a minimum of three runs, each at 16000 g for 15 min. Concentrations of CPT and DOX were determined via absorbance at 366 nm and 480 nm, respectively, of formulation serial dilutions utilizing a Tecan Infinite M200 Pro plate reader.

Results

A 1.6 mol % drug:HA ratio was achieved for both CPT-HA and DOX-HA conjugates. The drug encapsulation in CPT-HA-DOX was 5.9 mol % for CPT and 1.8 mol % for DOX.

Example 2. Cell Viability and Drug Combination Studies

Materials and Methods:

3-(4,5-Dimethylthiazol-2-yl)-2,5-diphenyltetrazolium bromide (MTT), from Thermo Fisher, DRAQ5, and Hoechst were purchased from Invitrogen Life Technologies. Breast cancer HER2-overexpressing cell line BT-474, mouse metastatic breast cancer cell line 4T1, mouse brain endothelial cell line bEnd.3, Hybri-Care medium, Dulbecco's Modified Eagle's medium (DMEM) and cell culture grade water were acquired from ATCC. Fetal bovine serum (FBS), phosphate buffered saline (PBS), RPMI-1640 media, 2-(N-morpholino)ethanesulfonic acid (IVIES) buffer, 0.25% trypsin, penicillin/streptomycin, and Nunc Lab-Tek 8-chambered cover glasses were purchased from Thermo Scientific. Cell culture flasks and microplates were purchased from Corning (NY, USA). Microcentrifuge filter tubes were purchased from EMD Millipore (Billerica, MA, USA).

Cell Culture

All cell lines were grown in a humidified incubator with 5% $CO_2$ at 37° C. BT-474 cells were cultured in Hybri-Care medium supplemented with 10% FBS, and 4T1 cells were cultured in RPMI-1640 medium supplemented with 10% FBS and 1% penicillin/streptomycin. Endothelial cell line bEnd.3 was cultivated in DMEM medium supplemented with 10% FBS and 1% penicillin/streptomycin.

Cell Viability and Drug Combination Studies in BT-474 and bEnd.3 Cells

BT-474 or bEnd.3 cells were seeded in a 96-well cell culture plate at a density of 10,000 cells per well in a total volume of 100 μL/well and allowed to adhere overnight. Media was then replaced with fresh media containing drug(s). Drugs were first dissolved in DMSO, and then further diluted in full cell culture medium so as not to expose cells to more than 0.5 vol % DMSO. BT-474 cells were incubated with drug solutions for 72 hours, while bEnd.3 cells were exposed to drug solutions for 48 hours. Drug incubation times were chosen such that all untreated cells, regardless of cell line, displayed similar absorbance values after MTT metabolization. To assess cell viability, the media was replaced with 0.5 mg/mL MTT in media and allowed to incubate for 4 hours. Media was aspirated and replaced with dimethyl sulfoxide (DMSO) to solubilize intracellularly reduced MTT (formazan crystals). Formazan dye intensity was determined by absorbance measured at 570 nm in a Tecan Infinite M200 Pro plate reader (Männedorf, Switzerland). The fraction of inhibited cell growth was calculated by subtracting live cells in experimental wells from untreated control cells and normalizing against control cells. D50 refers to the concentration of drug required to inhibit 50% cell growth. Experimental cytotoxicity data were fitted to the median-effect model developed by Chou and Talalay to obtain in vitro cytotoxicity curves for each drug.

Results

Synergistic Activity of CPT and DOX in Human Breast Cancer Cells

CPT and DOX were tested for synergistic cell growth inhibition of human breast cancer cell line BT-474 after 72 hour exposure (FIG. 1A). Synergy was quantified as the Combination Index (CI) (Chou, Pharmacol Rev, 2006. 58(3): 621-81); CI values lower than 1 indicate synergy whereas values greater than 1 imply antagonism. CI decreased with increasing molar ratio (R) of drugs, with the greatest synergy occurring when R (CPT:DOX)>2 (0.01<CI<0.08). The highest CI was 1±0.07, indicating that CPT and DOX interactions were never worse than additive.

Figure 2A:
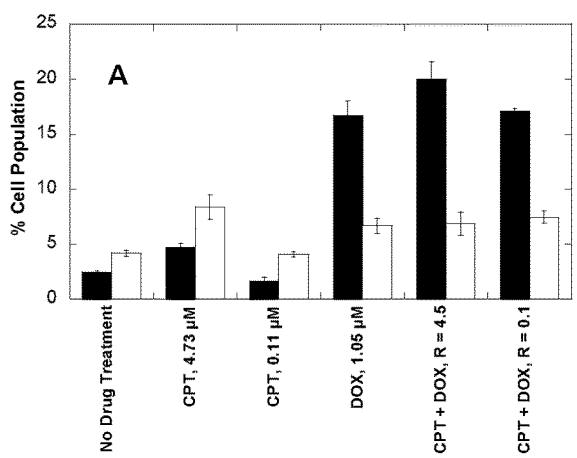
FIG. 2A is a bar graph showing the percentage of apoptotic cells in various drug-treated BT-474 cells. Cell populations were quantified via flow cytometry as follows: early apoptotic (black bars), and necrotic and/or late apoptotic (white bars).
Figure 2B:
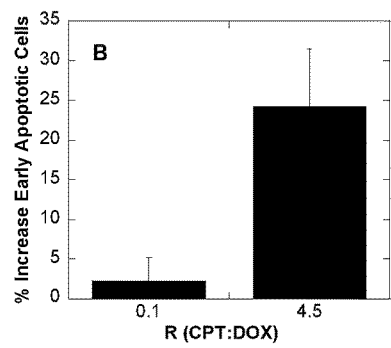
FIG. 2B displays the percent enhancement of early apoptotic cells relative to treatment with DOX alone.

CPT and DOX were identified as highly synergistic with low CI values, and were chosen as a model combination for HA-conjugation. For molar ratios >2 CPT:DOX, CI values were found to range between 0.01-0.1 (FIG. 1B). These values are among the lowest, and therefore most synergistic, of reported drug interaction studies evaluated by the CI method, rendering the pair highly desirable for co-delivery to tumors. Previous reports found CPT and DOX to be only additive in wild type rat C6 glioma cells, but slightly synergistic in a CPT-resistant C6 cell line (Pavillard, et al., Br J Cancer, 2001. 85(7): p. 1077-83). BT-474 human breast cancer cells which were utilized in this study were found to be inherently resistant to CPT, with a D50 of 100 μM, nearly 50 times that of CPT-resistant C6 cell lines reported in the literature. However, when BT-474 cells were treated with CPT and DOX at a molar ratio of R=4.5, the pair was able to inhibit 95% cell growth at a CPT concentration 100-fold less than the D50 (FIG. 1A). Furthermore, this synergistic combination induced >20% increase in pre-apoptotic cells compared to either single drug treatment (FIG. 2), thereby significantly improving efficacy at low drug concentrations In contrast, CPT and DOX exhibited antagonism when exposed to bEnd.3 endothelial cells. The combination, regardless of ratio, reduced the toxicity of CPT or DOX, as indicated by improved endothelial cell viability (FIG. 1C). The combination consistently inhibited less endothelial cell growth than CPT or DOX alone, suggesting that pair is far more toxic to cancer cells than endothelial cells.

Synergy of CPT- and DOX-Conjugated HA

CPT-HA and DOX-HA were mixed at various molar ratios and incubated with BT-474 cells. The combination inhibited more cancer cell growth than either CPT-HA or DOX-HA alone (FIG. 5A). The CI of the mixed conjugates (FIG. 5b) was less than 1 for 1<R<9 CPT:DOX, indicating that CPT-HA and DOX-HA were indeed synergistic at the same ratios that free CPT and DOX elicited synergy (FIGS. 1B and 1D).

CPT and DOX were then co-conjugated to HA. For the purpose of demonstrating a synergistic drug-loaded carrier, HA carrying a molar ratio of R=3.2 CPT:DOX was investigated. In vitro cytotoxicity studies show that CPT-HA-DOX inhibited more cancer cell growth than either CPT-HA (FIG. 6A) or DOX-HA (FIG. 6B) alone. Cell inhibition studies performed with mixed drug HA-conjugates and drugs co-conjugated to HA reveal that polymer-conjugation preserved synergy between CPT and DOX. While both compositions conserved the drug pair's potency, only the latter can ensure simultaneous exposure to tumor cells, and can provide a means to capture the in vitro antitumor efficacy in vivo, as well.

Example 3. Annexin V/Sytox Green Apoptosis Assay

Materials and Methods

Apoptosis assessment was made based on Annexin V and Sytox Green counterstaining. Studies followed the Life Technologies Apoptosis Assay protocol, with few modifications tailored to BT-474 cells. Briefly, cells were seeded at a concentration of $100 \times 10^4$ cells per 25 cm² cell culture flask in a total volume of 10 mL media, and allowed to adhere overnight. Media was then decanted and replaced with fresh media containing drug(s). Drugs were first dissolved in DMSO and further diluted in media such that cells were not exposed to more than 0.2 vol % DMSO. Cells were incubated in the presence of drug(s) for 72 hours. After drug exposure, cells were harvested at a concentration of $1 \times 10^6$ cells/mL in Annexin V binding buffer, and 200 µL of each sample were incubated with 5 µL of Annexin V-647 and 1 µL of 1 µM Sytox Green. After 15 minutes of dye incubation, cells were diluted 5× in ice cold Annexin V Binding Buffer, and immediately analyzed via flow cytometry in a Becton Dickinson FACSAria cell sorter (Franklin Lakes, NJ, USA). To quantify Annexin V-647 and Sytox Green fluorescence, a 633 nm laser with 660 PMT and a 488 nm laser with 530 PMT, respectively, were utilized. Cells gated as −AV/−SG were live, cells with +AV/−SG were pre-apoptotic, and cells gated as +AV/+SG were either late apoptotic or necrotic.

Results

Flow cytometry data indicated a 24% increase in early apoptotic population exposed to CPT+DOX (R=4.5, CI=0.05±0.01) compared to the treatment with DOX alone (FIG. 2), whereas cells exposed to additive ratio R=0.1 resulted in a 2% increase. Cells exposed only to CPT exhibited low percentages of apoptotic cells, incomparable to those treated with DOX alone, likely due to BT-474's inherent resistance to CPT. Since CPT and DOX inhibit Top I and II, respectively, exposure of either drug to cancer cells results in DNA damage and can induce apoptosis (Walton, et al., Cancer Res, 1993. 53(8): 1853-61).

Scatter plots obtained from flow cytometry of AnnexinV/Sytox Green counterstained cells were analyzed. These plots were utilized to quantify early apoptotic and late apoptotic/necrotic populations in FIG. 2. Cells stained with low levels of Annexin V and Sytox Green (−AV/−SG) were live, with high levels of Annexin V and low levels of Sytox Green (+AV/−SG) are early apoptotic, and high levels of both are necrotic and/or late apoptotic.

Example 4. Internalization Studies

Materials and Methods

To assess the effect of HA-conjugation on the internalization of CPT or DOX in BT-474 cells, confocal laser scanning microscopy was utilized. Cells were seeded at a density of 80,000 cells per 300 µL media in an 8-well chambered borosilicate coverglass (Nunc Lab-Tek), and were allowed to adhere overnight. Cells were exposed to the same drug concentration, the free drug $D_{50}$, of either the free drug solution or the HA-conjugate form for 24 hrs at 37° C. and 5% $CO_2$. Post-drug incubation, cells were washed twice with warmed PBS (pH 7.4), followed by staining with nuclear dyes at 37° C., 5% $CO_2$. In the case of DOX-exposed cells, Hoechst nuclear dye was utilized at a concentration of 25 µg/mL for 30 minutes. For CPT-exposed cells, to avoid overlap fluorescence between CPT and nuclear marker, DRAQ5 was used to stain nuclei at a concentration of 5 µM in media for 60 minutes. Cells were washed twice more in warm PBS and finally suspended in media immediately prior to imaging. All cells were imaged live with an Olympus Fluoview 1000 spectral confocal equipped with a 60× silicon oil objective and a 37° C. temperature-controlled imaging chamber. DOX, CPT, Hoechst and DAPI were excited with the following lasers: 488 nm 10 mW Argon gas (DOX), 405 nm 50 mW diode (CPT or Hoechst), and 635 nm 20 mW diode (DRAQ5). Z-stacks of 10 µm were captured and subsequently analyzed with ImageJ 1.47h software (NIH). Each z-stack was collapsed into an averaged image, and fluorescence intensity was reported as the raw integrated density divided by number of cells. An average of 25 cells was imaged in each field view.

HA internalization studies were conducted similarly. HA-Fluorescein (HA-F) of 250 kDa MW was purchased from Creative PEGWorks and directly dissolved in PBS, pH 7.4. The polymer was diluted in media, and incubated with BT-474 cells for 6 hours. To evaluate the need for energy-intensive internalization, cells were incubated at either 37° C. or 4° C. Hoechst was used to label cell nuclei. HA-F was excited at 488 nm, and analysis was performed, as described above.

Results

Figure 8:
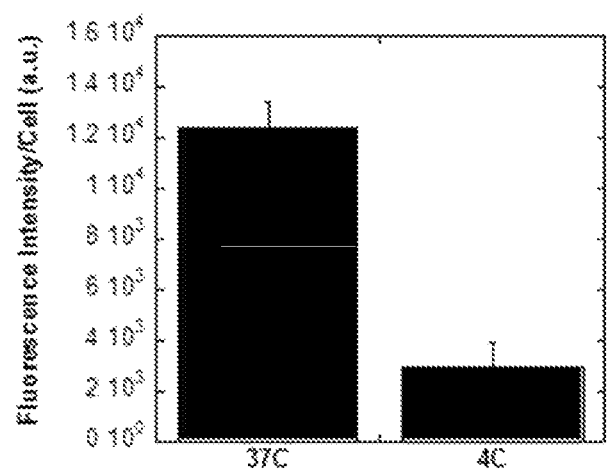
FIG. 8 is a bar graph showing the amount of internalization of fluorescein-conjugated HA in BT-474 cells at 37° C. and 4° C. Fluorescence was quantified in averaged 10 z-stacks, and was normalized to cell count per image.
Figures 9A, 9B, 9C, 9D:
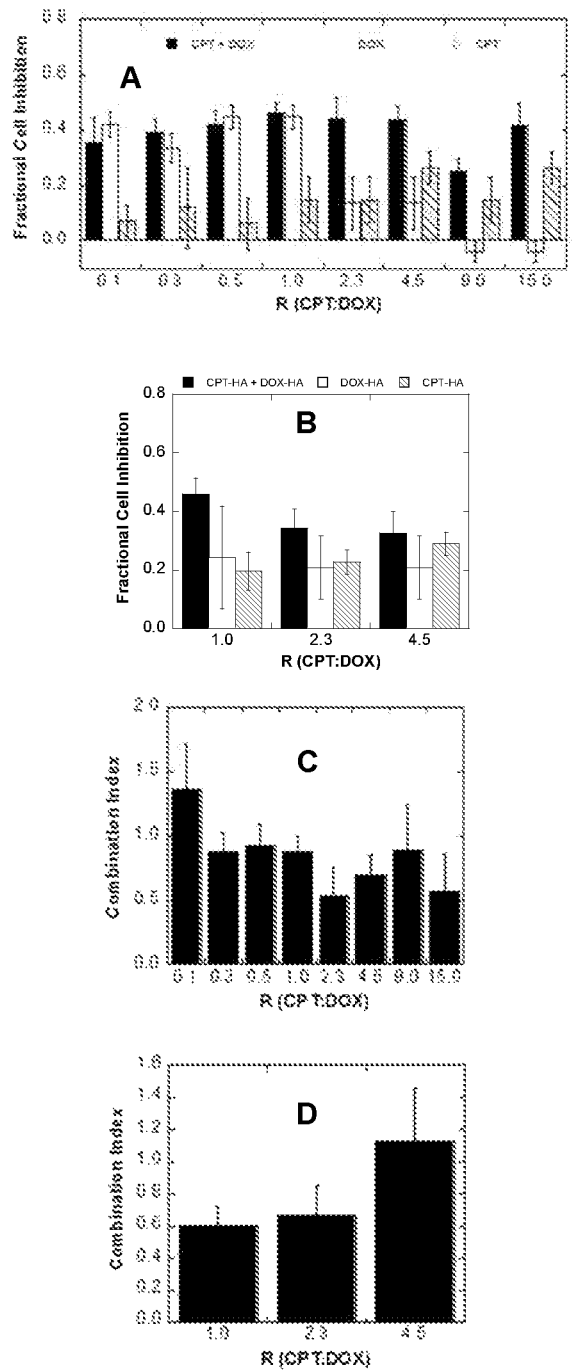
FIGS. 9A and 9B are bar graphs showing the cell inhibition of cancer cell line 4T1 exposed to free CPT+DOX and CPT-HA+DOX-HA, respectively.
FIGS. 9C and 9D display the combination index (CI) values for the CPT and DOX combinations in 4T1 cells.
Figure 10A:
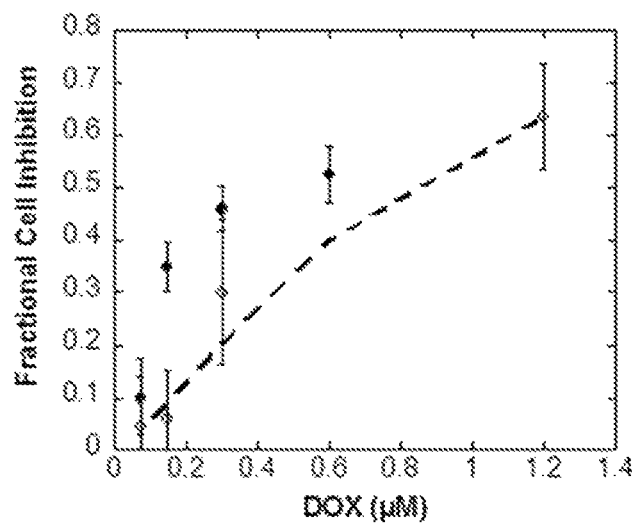
FIGS. 10A and 10B are bar graphs of cell inhibition studies comparing activity of single drug conjugates (blank circles) to CPT-HA-DOX (filled circles).
Figure 10B:
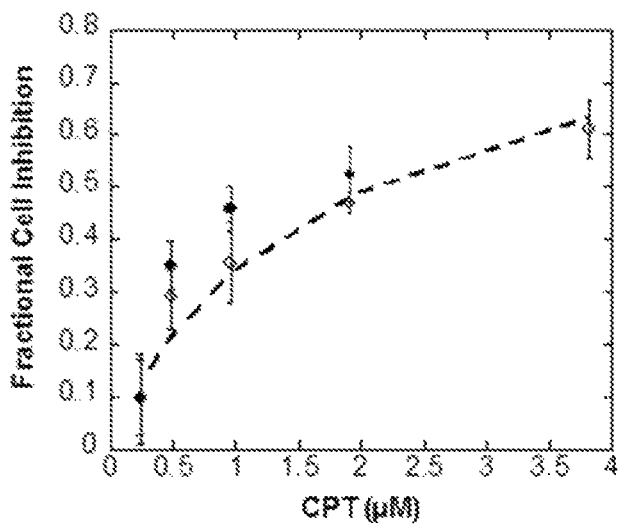

Internalization studies were performed to investigate the origins of shifts in drug activity upon HA conjugation. HA was internalized by an active process as confirmed by lack of internalization at 4° C. (FIG. 8). CPT-HA exhibited significantly enhanced uptake compared to free CPT (FIG. 4A) possibly due to its enhanced water solubility upon conjugation to HA. Uptake of DOX-HA on the other hand was comparable to that of free DOX. Subsequent intracellular distribution of HA-DOX, however, was significantly different compared to that of free DOX. HA-bound DOX was localized mostly in punctate spots surrounding nuclei, whereas free DOX was more diffuse and co-localized with cell nuclei.

Example 5. In Vivo Anti-Tumor Efficacy

Materials and Methods

An orthotopic 4T1 breast cancer mouse model in BALB/c mice was utilized to assess the in vivo anticancer efficacy of CPT-HA-DOX. A 4T1 model was chosen for its robust tumor formation in mice (Pulaski and Ostrand-Rosenberg, Curr Protoc Immunol, 2001. Chapter 20(2): Unit 20 2), and to challenge the synergistic conjugate with a highly metastatic, aggressive cancer (Fantozzi. and Christofori, Breast Cancer Res, 2006. 8(4): 212). All experiments were performed according to approved protocols by the Institutional Animal Care and Use Committee of the University of California, Santa Barbara. Six to eight week old female BALB/c mice were purchased from Charles River Laboratories (Wilmington, MA, USA). Tumor inoculation was achieved by subcutaneously injecting $5 \times 10^4$ 4T1 cells in the abdominal mammary gland in order to prevent interference with normal bodily functions. Prior to injection, 4T1 cells were washed twice in PBS and re-suspended in sterile 0.9 wt/vol % NaCl. Mice were randomly assigned to experimental and control groups, and were treated every other day with specified formulations beginning on day 3 post-inoculation, for a total of five treatments (Days 3, 5, 7, 9, 11). Mice were treated with i.v. tail injections of either CPT-HA-DOX or free CPT+DOX in equivalent drug doses of 2 mg/kg CPT and 1.05 mg/kg DOX. To prepare the free drug formulation, CPT was first dissolved in 10 vol % Tween-80 in 0.9 wt/vol % NaCl. DOX was directly dissolved in 0.9 wt/vol % NaCl, and was subsequently mixed with the CPT solution. CPT-HA-DOX was freshly prepared in 0.9% NaCl prior to injections. Tumor growth inhibition was assessed with tumor volume, quantified by $V = \frac{1}{2}(l) \times (w)_2$, where 1 is the longest tumor diameter and w is the shortest tumor diameter measured by a digital caliper.

Results

Figures 7A, 7B:
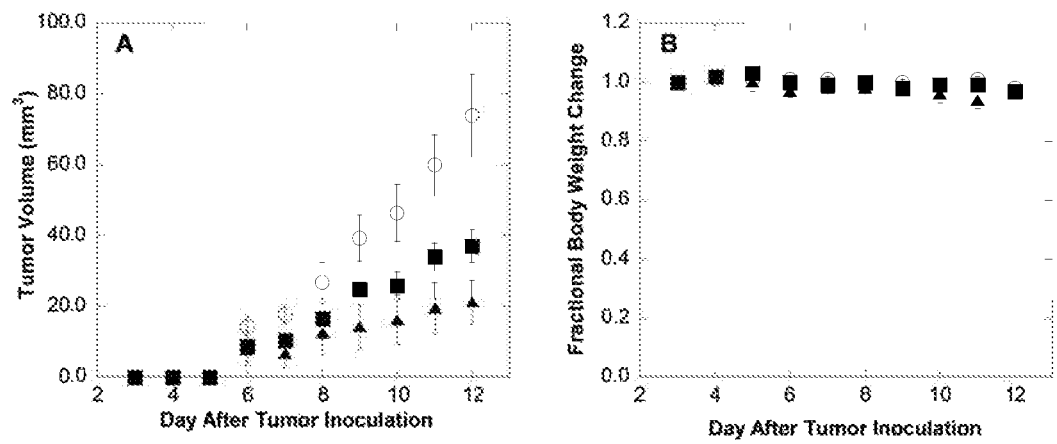
FIG. 7A displays the tumor growth of mice bearing 4T1 breast cancer tumors, without treatment (open circles), with IV injections of CPT-HA-DOX (filled squares), or free CPT+DOX in 0.9% saline (filled triangles).
FIG. 7B displays the change in body weight of control mice (open circles), CPT-HA-DOX-treated mice (filled squares), or CPT+DOX-treated mice (filled triangles).

While all in vitro studies focused on the cell inhibition of BT-474 human breast cancer cells, CPT and DOX synergy was also verified in 4T1 cells and occurred at the same ratios as BT-474 (FIGS. 9A-10B). Mice were administered i.v. with designated formulations every other day for a total of 5 treatments. As high as 70% tumor volume reduction was achieved by the free drug combination (FIG. 7A), and 50% tumor reduction was achieved with the co-conjugated polymer relative to control. In both cases, negligible body weight change was observed (FIG. 7B).

Example 6. In Vivo Toxicity

Methods and Materials

Caspase-3 immunohistochemistry and hematoxylin and eosin (H&E) histology analyses were also performed on excised tumors post-treatment in order to further assess tumor growth inhibition. Tumors were fixed and further sent to Mass Histology Services, Inc., where the tissues were paraffin-blocked, stained, and analyzed. To evaluate formulation toxicity, body weights were measured daily. Additionally, liver, spleen, heart, and lung organs were harvested at the end of the experiments, fixed and further analyzed by Mass Histology Services, Inc. (Worcester, MA, USA) via H&E staining. Histology analyses of mice treated with free and HA-conjugated CPT+DOX were conducted to assess formulation toxicity. Heart, lung, spleen, and liver organs were harvested post-treatment, immediately fixed in 10% formaldehyde, and further stored in 70% ethanol. Histology preparation and H&E staining were acquired at 100× magnification and are representative of each group (n=3).

Results

Caspase 3 immunohistochemistry of tumor sections post-treatment was performed to further assess antitumor efficacy of CPT and DOX formulations. Despite greater gross tumor reduction in mice treated with free CPT+DOX, more apoptotic cells were found in CPT-HA-DOX-treated tumors. H&E staining showed more necrosis in mice treated with CPT-HA-DOX compared to those treated with free CPT+DOX. Histology analyses suggest that, while macroscopic measurements indicate that free CPT+DOX mixture is more effective in reducing tumor size, CPT-HA-DOX was more effective in inducing both necrosis- and apoptosis-induced cell death. Histology analyses of essential organs post-treatment were conducted to further investigate formulation toxicity. Lung, spleen, and liver organs in both CPT+DOX-treated and CPT-HA-DOX-treated mice showed no toxicity. Heart sections resected from CPT-HA-DOX-treated mice indicated mild inflammation, whereas those from CPT+DOX-treated mice showed no toxicity. Overall, both formulations were well-tolerated with no severe side effects. Comparisons between untreated, CPT-HA-DOX-treated, and free CPT+DOX-treated mice show no treatment-related toxicity in lung, spleen and liver organs. Mild inflammation was found in the heart of CPT-HA-DOX-treated mice, whereas normal heart staining was observed in free CPT+DOX-treated mice. Overall, both free and HA-conjugated methods demonstrated minimal toxicity and were well tolerated.

Example 7. Effects of Drug Delivery Schedule on Synergy

Materials and Methods

Doxorubicin HCl (DOX), gemcitabine HCl (GEM), paclitaxel (PAC), ixabepilone (IXA), and lapatinib di-p-toluenesulfonate salt (LAP) were purchased from LC Laboratories (Woburn, MA, USA). Hyaluronic acid (HA) of 250 kDa MW was purchased from Creative PEGWorks (Winston Salem, NC, USA). MTT was purchased from Thermo Fisher. DMSO was purchased from Sigma Aldrich.

Cell Viability Assays

MDA-MB-231 cells (ATCC) were cultured in RPMI 1640 media supplemented with 10% FBS and 1% PS. MCF-10a cells (ATCC) were cultured in MEGM complete media (excluding GA-1000) supplemented with 100 ng/mL cholera toxin. For cell viability assays, MDA-MB-231 and MCF-10a cells were seeded at a density of 5000 cells per well in a 96 well plate. The following day, media were removed, and media with a first drug was added. Depending on the schedule being tested, a second drug (which was different from the first drug) was added at later time points by removing all of the media in the wells (which contained the first drug), and adding to the well new media, which contained the second drug. At the end of the study (typically 72 hr), media (which contained the second drug) were replaced with MTT reagent in media (0.5 mg/mL). After incubating the cells for 4 hours with MTT, the media were removed and replaced with DMSO. After 30 minutes of shaking, absorbance was read on a plate reader at 570 nm.

Two classes of schedules were tested: concurrent exposure, involving current exposure of the cells to a first and second drug; and sequential exposure, involving exposure of the cells to a first drug for a first time period, followed by exposure of the cells to a second drug for a second time period.

Schedules that were tested for concurrent exposure involved concurrent exposure of cells to a first drug and a second drug for the whole three-day period. Schedules that were tested for sequential exposure involved exposure of cells to a first drug for 4, 12, 24, or 36 hrs, followed by exposure of the cells to a second drug for 68, 60, 48, or 36 hrs, respectively.

Results

Figure 11A:
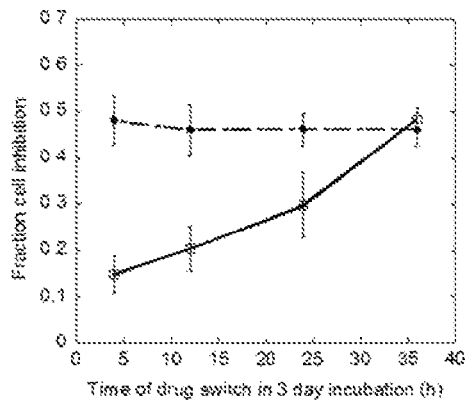
FIGS. 11A-11C are line graphs of fractional cell inhibition on MDA-MB 231 cells as a function of drug sequence (Drug 1→Drug 2) and time at which the switch occurred during a three-day incubation period.
Figure 11B:
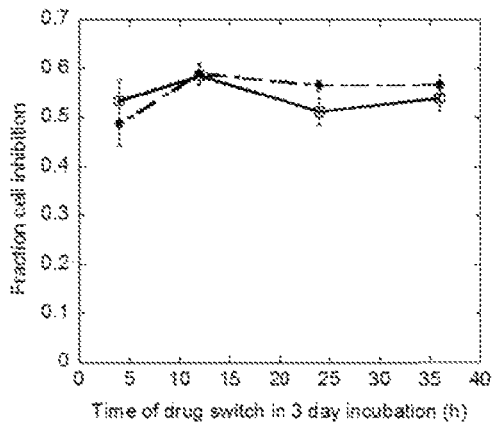
Figure 11C:
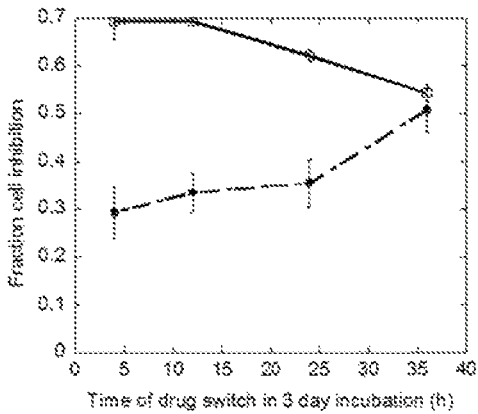

The effect of drug delivery schedule on synergy was observed experimentally by quantifying cell inhibition as a function of different drug administration schedules. Each drug pair had a unique relationship between drug delivery schedule and synergy. For example, fraction cell toxicity is shown for three different drug pairs (utilizing doses near the IC50's of the individual drugs) in MDA-MB 231 cells as function of the time in which the cells were exposed to a second drug (FIG. 11). While some drug pairs show a significant effect of schedule on cell toxicity (DOX/PAC and DOX/GEM), drug delivery schedule does not play a significant role for other drug pairs (PAC/IXA).

Figure 12A:
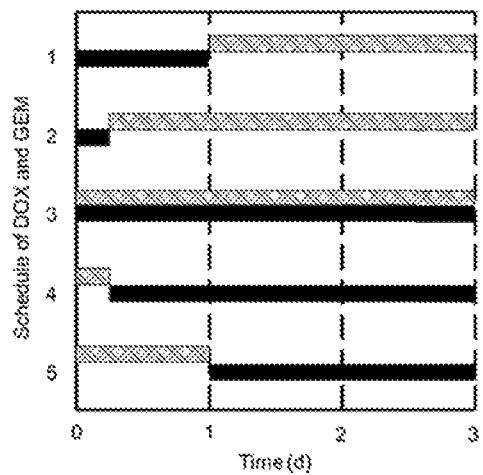
FIGS. 12A-12C are bar and column graphs of the effects of schedule on synergy between DOX (0.3 μM) and GEM (0.3 μM) on MDA-MB 231 cells.
Figure 12B:
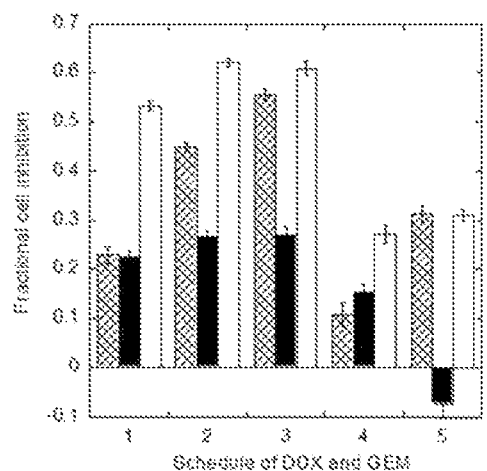

To determine the effect of schedule on synergy, individual drugs need to be screened at the exact same schedules as those in the combination, because each drug has its own unique pharmacodynamics. For example, triple negative breast cancer cells (MDA-MB 231) were exposed to various schedules of combinations of DOX and GEM, and the individual drugs (FIG. 12). The combination index (CI) for each drug administration schedule was calculated using the Chou-Talalay method. For each respective schedule, the CI value utilized dose response curves of the free drugs generated at the same schedule of administration, as shown for one specific dose in FIG. 12B.

Figure 12C:
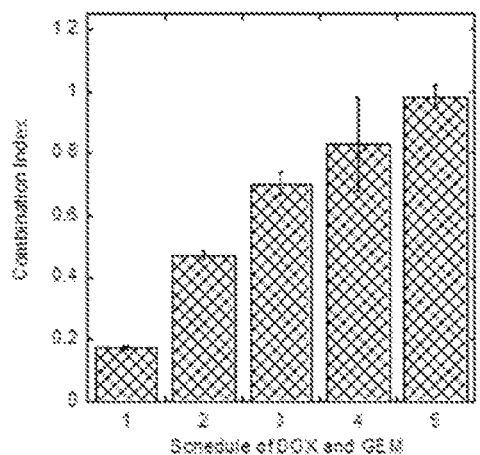

While DOX and GEM are synergistic when given concurrently for three days (CI<1), the degree of synergy significantly increases when GEM is given prior to DOX (FIG. 12C). The opposite effect is observed when DOX is given prior to GEM.

When designing a combination polymer-drug conjugate with DOX and GEM, the strength of the chemical linkers preferably allows for GEM to release faster than DOX.

While designing a polymer-drug conjugate for combination therapy, both schedule and molar ratio should be considered with respect to cancer and healthy cell toxicity. The degree of synergy was compared at the most synergistic schedule for MDA-MB 231 cells (GEM (1d) DOX→(2d)) to a healthy breast epithelial cell line (MCF-10a). Utilizing drug doses near the IC50 in both cell lines, the CI was calculated as a function of molar ratio between DOX and GEM.

Figure 13:
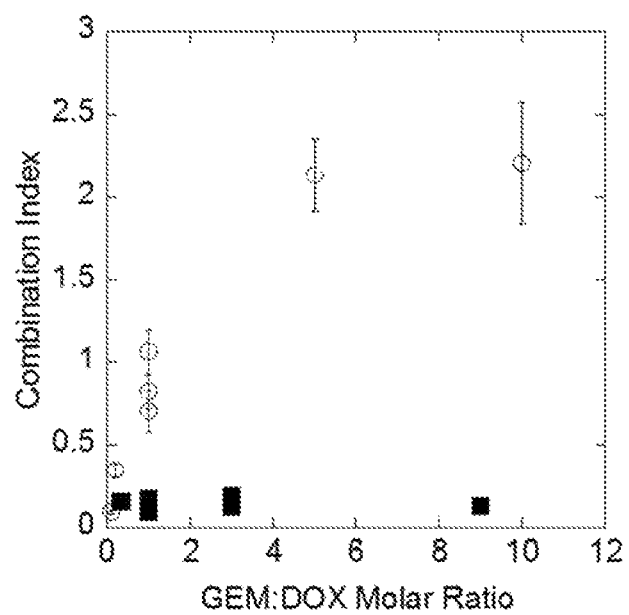
FIG. 13 is a scatter plot showing the degree of synergy, expressed as combination index, for sequential delivery of GEM (1d) to DOX (2d) in triple negative breast cancer cells (MDA-MB231—filled squares) and healthy breast epithelial cells (MCF-10a—open circles) as a function of GEM:DOX molar ratio.

The sequential delivery of GEM to DOX is significantly more synergistic in the cancer cells than healthy cells at GEM:DOX molar ratios greater than 0.3. This difference is enhanced as GEM is given in excess of DOX (FIG. 13).

Figure 14A:
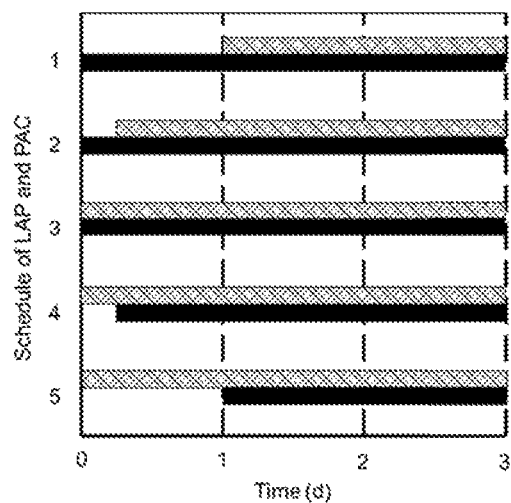
FIGS. 14A and 14B are bar and column graphs of the effects of schedule on synergy between paclitaxel (PAC, at 0.01 μM) and lapatinib (LAP, at 0.03 μM) on BT-474 cells.
Figure 14B:
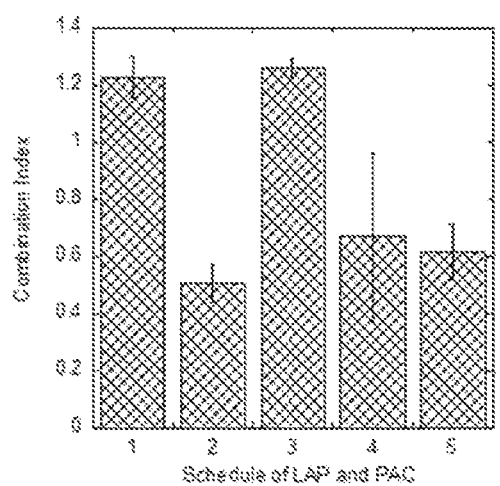

Different results were observed when LAP and PAC were delivered to the HER2+ breast cancer cell line BT-474. For example, delivering LAP 4 h prior to PAC and delivering PAC 4 h prior to LAP is synergistic; however, delivering the two drugs concurrently is antagonistic on the HER2+ breast cancer cell line BT-474 (FIG. 14).

Example 8. Synthesis of DOX-HA and GEM-HA Conjugates

Materials and Methods

Doxorubicin HCl (DOX), and gemcitabine HCl (GEM) were purchased from LC Laboratories (Woburn, MA, USA). Sodium hyaluronate (250 kDa MW, 10 mg/mL) was purchased from Creative PEGWorks (Winston Salem, NC, USA). N,N,N',N'-Tetramethyl-O-(benzotriazol-1-yl)uronium tetrafluoroborate (TBTU), 1-Ethyl-3-(3-dimethylaminopropyl)carbodiimide (EDC) HCl, BOC-glycine, anhydrous DMF, DMSO, ethyl acetate, DIPEA, methanol, sodium bicarbonate, DCM, TFA, and SiO2 resin were purchased from Sigma Aldrich.

(i) DOX-HA Conjugates

DOX was conjugated to HA through various bonds, varying in strength, which allows for release of the agent (DOX) at different times.

(a) DOX-HA Imine

Figure 15A:
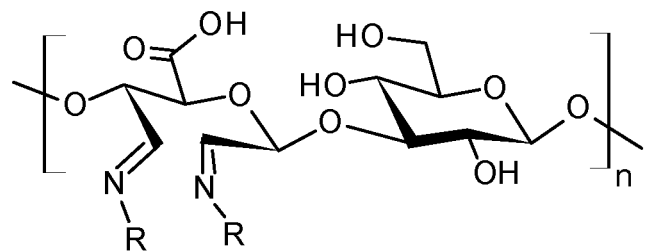
FIGS. 15A-15C are schematic diagrams showing the different strategies that a drug (R), such as DOX, GEM, or another agent, can be conjugated to a polymer such as hyaluronic acid.

The vicinal diol group on HA can be oxidized with NaIO4 to produce aldehydes which react with the primary amine group on DOX to form an imine (FIG. 15A).

Sodium hyaluronate (250 kDa, 10 mg/mL) was dissolved into deionized water and mixed with sodium periodate (5 mol % relative to disaccharide repeat unit) and stirred in the dark for 4 hours at room temperature to oxidize the vicinal diol group to aldehydes. The oxidized polymer was purified with dialysis and lyophilization. Then, the polymer was dissolved into 5 mM phosphate buffer at pH 6 (10 mg/mL) and mixed with DOX·HCl (5 mol % relative to disaccharide repeat unit). The product was precipitated and washed with acetone, and then further purified with dialysis. The imine was completely hydrolyzed in acidic conditions of pH 5 in approximately one day.

(b) DOX-HA Hydrazine

Figure 15B:
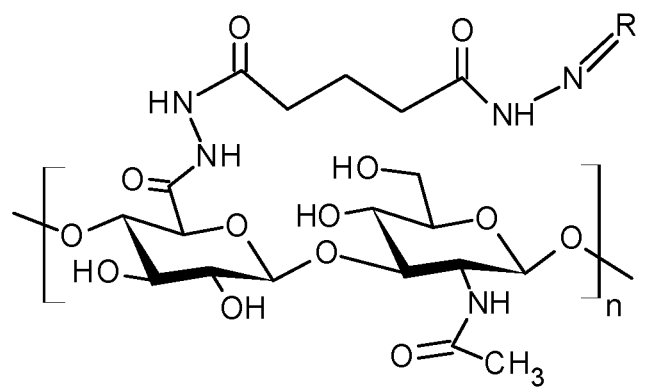

The carboxylic acid group on HA can be coupled to adipic acid dihydrazide, which reacts with the ketone on DOX to form a hydrazone (FIG. 15B), which is also quickly hydrolyzed in acidic conditions.

The general synthesis used in this example was adapted from previous reports (Cai, et al., Journal of Controlled Release 2010, 146(2), 212-218). Briefly, sodium hyaluronate (250 kDa, 10 mg/mL) was dissolved in deionized water and mixed with an equimolar amount of adipic acid dihydrazide (ADH). EDC·HCl was added in the powder form (10 mol % relative to disaccharide repeat unit) and the reaction was stirred at room temperature overnight. The product was precipitated and washed with acetone. Then the product (HA-ADH) was dissolved into 5 mM phosphate buffer at pH 6.5 (10 mg/mL) and mixed with DOX·HCl (5 mol % relative to disaccharide repeat unit) and stirred overnight at room temperature. Again, the product was isolated by precipitating and washing in acetone followed by dialysis.

(c) DOX-HA Amide

Figure 15C:
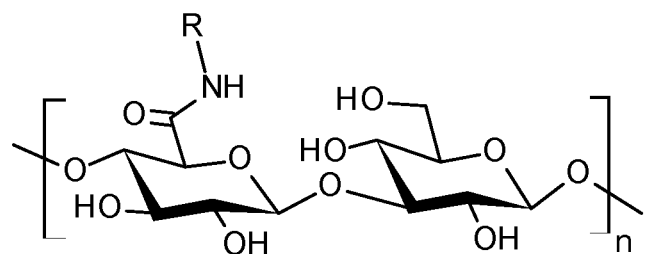

Lastly, a strong amide bond can be formed by directly conjugating the amine on DOX to the carboxylic acid on HA (FIG. 15C).

The general synthesis used in this example was been previously reported (Oomen, et al., Macromolecular Bioscience 2014, 14, 327-333). Briefly, sodium hyaluronate (250 kDa, 10 mg/mL) was dissolved in deionized water and mixed with DOX·HCl (5 mol % relative to disaccharide repeat unit). EDC·HCl was then added in the powder form (5 mol % relative to disaccharide repeat unit) and the reaction was stirred at room temperature overnight. The product was precipitated and washed with acetone, and then further purified with dialysis.

(ii) GEM-HA Conjugates

HA-GEM conjugates can also be formed with a wide range of bond strengths. Because the amine group on GEM is much less reactive than that of DOX, a GEM-glycine prodrug is typically synthesized to increase the amount of the drug conjugated to HA. Two different versions of the prodrug were formed in this Example to vary the release rate of the active form of GEM from GEM-glycine (FIG. 16).

The prodrug can be synthesized by coupling the carboxylic acid on BOC-protected glycine to the amine or alcohol groups on GEM to form an amide or ester, followed by BOC deprotection. The GEM-glycine prodrug can then be conjugated to HA utilizing the amine group on glycine to form an imine or amide, as shown in FIGS. 15A and 15C, respectively.

(a) GEM-Glycine Amide

Figure 16B:
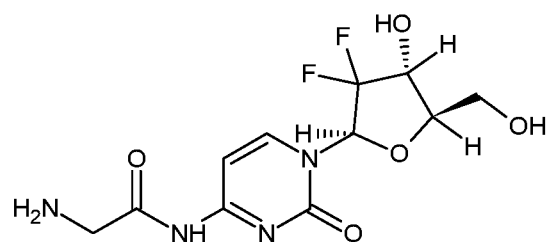
Figure 16C:
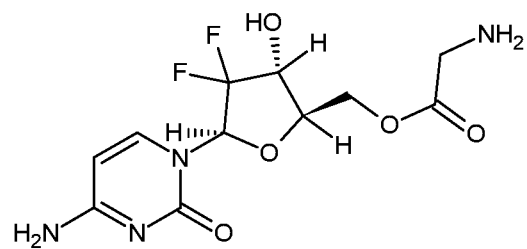

BOC-glycine was mixed with an equimolar amount of N,N,N',N'-Tetramethyl-O-(benzotriazol-1-yl)uronium tetrafluoroborate (TBTU) and DIPEA (1.5 molar eq) in anhydrous DMF. GEM·HCl was dissolved into anhydrous DMF with an equimolar amount of DIPEA. After the carboxylic acid on BOC-glycine was activated for 30 minutes, BOC-glycine was added dropwise to the GEM solution. The reaction was stirred for 1 hr, and then the majority of DMF was removed by rotary evaporation. The BOC-glycine-GEM amide was isolated by extraction into ethyl acetate with wash steps consisting of DI water, saturated sodium bicarbonate and brine, followed with SiO2 chromatography using an solvent eluent of 10:1.25 DCM:methanol. The BOC group was then deprotected in a 1:1 mixture of TFA:DCM, and solvent was then removed with rotary evaporation. A schematic of a GEM-glycine amide prodrug is shown in FIG. 16B.

(b) GEM-Glycine-HA Amide

Sodium hyaluronate was converted into the acidic form (HA) by mixing with an equimolar amount of HCl and isolated with lyophilization. HA was then dissolved into anhydrous DMSO (10 mg/mL) and mixed with TBTU (5 mol % relative to disaccharide repeat unit) and DIPEA (10 mol % relative to disaccharide unit). After stirring for 15 minutes, GEM-Glycine (5 mol % relative to disaccharide repeat unit) was added to the activated polymer. The polymer conjugate was isolated by precipitation and washing in ethyl acetate followed with further dialysis.

(c) GEM-Glycine-HA Imine

Sodium hyaluronate (250 kDa, 10 mg/mL) was dissolved into deionized water and mixed with sodium periodate (5 mol % relative to disaccharide repeat unit) and stirred in the dark for 4 hours at room temperature to oxidize the vicinal diol group to aldehydes. The oxidized polymer was purified with dialysis and lyophilization. Then, the polymer was dissolved into 5 mM phosphate buffer at pH 6 (10 mg/mL) and mixed with GEM-glycine (5 mol % relative to disaccharide repeat unit). After stirring for 4 hr, the product was isolated by precipitation and washing with acetone followed with dialysis.

We claim:

1. A method of treating cancer in a patient comprising administering to the patient a pharmaceutical composition comprising doxorubicin and camptothecin conjugated to a biocompatible polymer;
wherein the doxorubicin and camptothecin are conjugated to the biocompatible polymer directly via covalent bonds or indirectly via linkers; and
wherein at least one of the doxorubicin and camptothecin are conjugated to the biocompatible polymer directly via covalent bonds.

2. The method of claim 1, wherein the molar ratio of doxorubicin to camptothecin is 1:1 or more doxorubicin.

3. The method of claim 2, wherein the molar ratio of doxorubicin to camptothecin is from 1:1 to 1000:1.

4. The method of claim 2, wherein the molar ratio of doxorubicin to camptothecin is from 1:1 to 10:1.

5. The method of claim 2, wherein the molar ratio of doxorubicin to camptothecin is 2:1 or more doxorubicin.

6. The method of claim 2, wherein the molar ratio of doxorubicin to camptothecin is 3.33:1 or more doxorubicin.

7. The method of claim 2, wherein the molar ratio of doxorubicin to camptothecin is 10:1.

8. The method of claim 2, wherein the molar ratio of doxorubicin to camptothecin is 2:1.

9. The method of claim 1, wherein the molar ratio of camptothecin to doxorubicin is 2:1 or more camptothecin.

10. The method of claim 9, wherein the molar ratio of camptothecin to doxorubicin is from 2:1 to 1000:1.

11. The method of claim 1, wherein the biocompatible polymer is hyaluronic acid.

12. The method of claim 1, wherein the bonds conjugating the doxorubicin to the biocompatible polymer directly or indirectly via linkers and the bonds conjugating the camptothecin to the biocompatible polymer directly or indirectly via linkers have bond strengths that are the same, different, or a combination thereof.

13. The method of claim 1, wherein the bonds conjugating the doxorubicin to the biocompatible polymer directly or indirectly via linkers and the bonds conjugating the camptothecin to the biocompatible polymer directly or indirectly via linkers have bond strengths that are the same.

14. The method of claim 1, wherein the bonds conjugating the doxorubicin to the biocompatible polymer directly or indirectly via linkers and the bonds conjugating the camptothecin to the biocompatible polymer directly or indirectly via linkers have bond strengths that are different.

15. The method of claim 1, wherein at least one of the doxorubicin and the camptothecin are indirectly conjugated to the biocompatible polymer.

16. The method of claim 1, wherein the concentration of each of doxorubicin and camptothecin in the composition is between about 0.001 µM and about 10 µM.

17. The method of claim 1, wherein the composition is in a form suitable for topical mucosal administration.

18. The method of claim 1, wherein an adverse side effect in the patient is reduced compared to the delivery of the same therapeutically active agents in the same doses and in an unconjugated form.

19. The method of claim 18, wherein the adverse side effect is hematological toxicity.

20. The method of claim 1, wherein the molar ratio of doxorubicin to camptothecin is from 1:2 to 1:1.

21. The method of claim 1, wherein the doxorubicin and the camptothecin are each directly conjugated to the biocompatible polymer.

22. The method of claim 1, wherein the doxorubicin and camptothecin are conjugated to the biocompatible polymer directly via covalent bonds to side chains of the biocompatible polymer or indirectly via linkers to side chains of the biocompatible polymer.

23. A method of treating cancer in a patient comprising administering to the patient a pharmaceutical composition comprising doxorubicin and camptothecin conjugated to a biocompatible polymer;
wherein the doxorubicin and camptothecin are conjugated to the biocompatible polymer directly via covalent bonds to side chains of the biocompatible polymer.

* * * * *